US010462495B2

(12) United States Patent
Hachfeld

(10) Patent No.: US 10,462,495 B2
(45) Date of Patent: Oct. 29, 2019

(54) PROGRESSIVE LOSSLESS COMPRESSION OF IMAGE DATA

(71) Applicant: Vital Images, Inc., Minnetonka, MN (US)

(72) Inventor: William D. Hachfeld, Apple Valley, MN (US)

(73) Assignee: Vital Images, Inc., Minnetonka, MN (US)

( * ) Notice: Subject to any disclaimer, the term of this patent is extended or adjusted under 35 U.S.C. 154(b) by 161 days.

(21) Appl. No.: 15/672,689

(22) Filed: Aug. 9, 2017

(65) Prior Publication Data

US 2019/0052913 A1 Feb. 14, 2019

(51) Int. Cl.
G06K 9/00 (2006.01)
H04N 19/93 (2014.01)
H04N 19/172 (2014.01)
H04N 19/91 (2014.01)
H04N 19/176 (2014.01)
H04N 19/593 (2014.01)
(Continued)

(52) U.S. Cl.
CPC ............. *H04N 19/93* (2014.11); *G16H 30/00* (2018.01); *H04N 19/172* (2014.11); *H04N 19/176* (2014.11); *H04N 19/184* (2014.11); *H04N 19/59* (2014.11); *H04N 19/593* (2014.11); *H04N 19/80* (2014.11); *H04N 19/90* (2014.11); *H04N 19/91* (2014.11)

(58) Field of Classification Search
None
See application file for complete search history.

(56) References Cited

U.S. PATENT DOCUMENTS 6,307,557 B1 * 10/2001 Deering ................. G06T 9/001
                                                                    345/428
7,376,279 B2    5/2008 Dekel et al.
(Continued)

OTHER PUBLICATIONS

"Delta encoding", Wikipedia, [Online]. Retrieved from the Internet: <URL: https://en.wikipedia.org/wiki/Delta_encoding>, (Accessed Sep. 12, 2017), 5 pgs.
(Continued)

*Primary Examiner* — Hadi Akhavannik
(74) *Attorney, Agent, or Firm* — Schwegman Lundberg & Woessner, P.A.

(57) ABSTRACT

Techniques and configurations for compression of image data in a progressive, lossless manner are disclosed. In an example, three-dimensional medical images may be compressed and decompressed with high-speed operations, through a compression technique performed on a cube (chunk) of voxels that includes generating a subsampled or filtered cube of voxels, and generating and optimizing a delta data set between the cube of voxels and the subsampled cube of voxels. This optimized delta data set is operable with a decompression technique to losslessly recreate the cube of voxels. Further, the compression technique may be progressively performed with multiple iterations, to allow multiple lower resolution versions of the images prior to loading or receiving the entire compressed data that is reconstructable in a lossless form. Use of this technique may result in dramatically reduced time to first image when visualizing 3D images and performing image data transfers.

31 Claims, 12 Drawing Sheets

(51) Int. Cl.
　　H04N 19/184　　(2014.01)
　　H04N 19/80　　(2014.01)
　　H04N 19/90　　(2014.01)
　　H04N 19/59　　(2014.01)
　　G16H 30/00　　(2018.01)

(56) References Cited

U.S. PATENT DOCUMENTS

| | | | |
|---|---|---|---|
| 7,676,102 B2 | 3/2010 | Sakai et al. | |
| 8,422,784 B2 | 4/2013 | Schneider | |
| 8,508,539 B2* | 8/2013 | Vlietinck | G06T 15/005 345/502 |
| 2004/0217956 A1* | 11/2004 | Besl | G06T 15/00 345/419 |
| 2005/0111746 A1 | 5/2005 | Kumar et al. | |
| 2006/0012597 A1* | 1/2006 | Chakraborty | G06K 9/00214 345/419 |
| 2006/0050972 A1* | 3/2006 | Reznic | H04N 19/593 382/232 |
| 2008/0232718 A1* | 9/2008 | Avinash | A61B 6/032 382/305 |
| 2009/0274350 A1* | 11/2009 | Pavlovskaia | G06K 9/32 382/128 |
| 2010/0128998 A1* | 5/2010 | Wegener | G06T 9/00 382/248 |
| 2015/0093023 A1* | 4/2015 | Greenebaum | G06T 9/00 382/166 |
| 2015/0235360 A1* | 8/2015 | Zheng | G06K 9/46 382/128 |
| 2016/0086353 A1* | 3/2016 | Lukac | G06T 9/00 345/419 |
| 2019/0139266 A1* | 5/2019 | Budagavi | G06T 9/001 |

OTHER PUBLICATIONS

"Dictionary coder", Wikipedia, [Online]. Retrieved from the Internet: <URL: https://en.wikipedia.org/wiki/Dictionary_coder>, (Accessed Sep. 12, 2017), 3 pgs.
"General Description of the NRRD format", Wikipedia, [Online]. Retrieved from the Internet: <URL: http://teem.sourceforge.net/nrrd/descformat.html>, (Accessed Sep. 12, 2017), 4 pgs.
"Nearly Raw Raster Data", Wikipedia, [Online]. Retrieved from the Internet: <URL: http://teem.sourceforge.net/nrrd/>, (Accessed Sep. 12, 2017), 2 pgs.
"Nearly Raw Raster Data—Introduction", Wikipedia, [Online]. Retrieved from the Internet: <URL: http://teem.sourceforge.net/nrrd/intro.html>, (Accessed Sep. 12, 2017), 3 pgs.
"Run-length encoding", Wikipedia, [Online]. Retrieved from the Internet: <URL: https://en.wikipedia.org/wiki/Run-length_encoding>, (Accessed Sep. 12, 2017), 3 pgs.
"SIMD", Wikipedia, [Online]. Retrieved from the Internet: <URL: https://en.wikipedia.org/wiki/SIMD>, (Accessed Sep. 12, 2017), 7 pgs.
"Two's complement", Wikipedia, [Online]. Retrieved from the Internet: <URL: https://en.wikipedia.org/wiki/Two's_complement>, (Accessed Sep. 12, 2017), 12 pgs.
"Z-order curve", Wikipedia, [Online]. Retrieved from the Internet: <URL: https://en.wikipedia.org/wiki/Z-order_curve>, (Accessed Sep. 12, 2017), 7 pgs.

* cited by examiner

PROGRESSIVE LOSSLESS COMPRESSION OF IMAGE DATA

TECHNICAL FIELD

Embodiments pertain to data processing techniques used for imaging data within information networks and informatics systems. Further embodiments relate to the use and application of compression techniques for two-dimensional and three-dimensional image data, including medical imaging data produced from medical imaging modalities.

BACKGROUND

As healthcare processes have become increasingly digitized, large volumes of patient data are now generated on human patients at nearly every medical facility for many types of healthcare interactions. This patient data includes significant amounts of medical imaging data that is captured by medical imaging modalities (e.g., an x-ray machine, computed tomography (CT) scanner, magnetic resonance imaging (MRI) machine, and the like). In many medical settings, image data is first captured by the imaging modality, and then later transferred via a network to another location such as a viewing workstation for further analysis, evaluation, or diagnosis by a healthcare provider.

One practical consideration relating to the use of medical imaging data involves the amount of time required to obtain and transfer the medical images over a network, to generate a view of the medical images at a viewing location. This time is often dependent on the network and processing capabilities and computational resources available to transfer and interpret the imaging data. For imaging applications that visualize separate two-dimensional (2D) images, this time may be quite short and is primarily a function of network latency. For more advanced applications that generate visualizations of three-dimensional (3D) images, however, an entire stack of images must typically be transferred before viewing and interacting with the visualizations.

As a result of these and other technical considerations, many transfers of medical imaging data are bandwidth sensitive, which has led to the increased use of compression for imaging data. However, some compression schemes are not appropriate for use with medical imaging use cases, particularly if the compression technique leads to the loss or obscuring of diagnostic detail in the image data. Further, the use of some compression schemes within medical imaging networks often involves a performance and processing overhead that may not result in sufficient savings in time or network resources.

DETAILED DESCRIPTION

Figure 1:
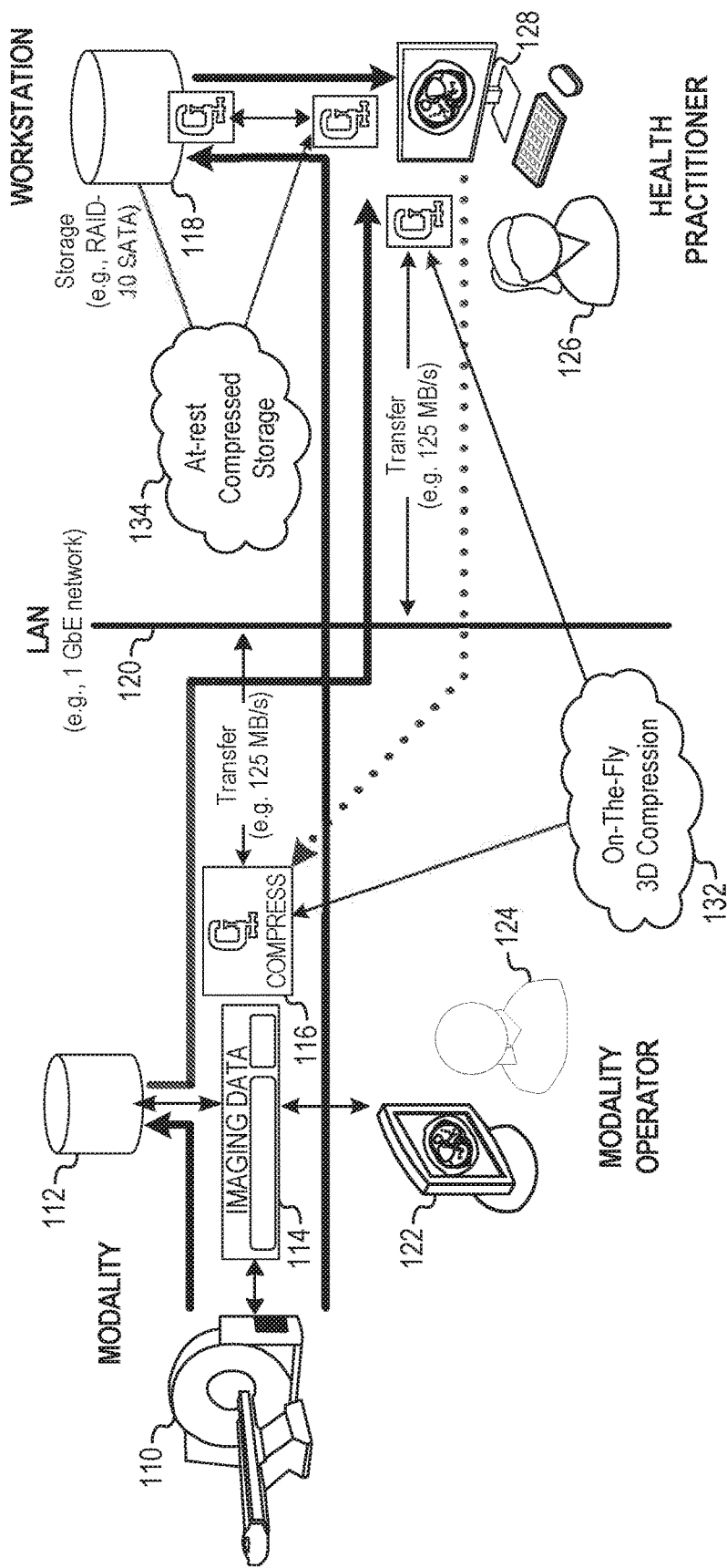
FIG. 1 illustrates a diagram of a system configuration for implementing progressive lossless compression of medical imaging data according to an example described herein.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments.

The present disclosure illustrates various techniques and configurations that enable compression and decompression of imaging data, including original and reduced-resolution forms within a progressive compression approach. The following operations may be used, for example, as a compression technique for a three-dimensional (3D) volume of image voxels. The following operations also may be used as a compression technique for a two-dimensional slab of image pixels, and for varying formats of two-dimensional and three-dimensional image data sets. Further, the following compression techniques may be implemented in connection with a variety of chunk sizes within such image data sets, including various types of N×N×N chunks of voxels (where N is a power of 2).

In the examples further detailed below, the operation of this progressive compression technique may be implemented through the use of resolution subsampling, delta encoding, and optimizations of deltas among different resolution versions. The compression technique supports high-speed compression of 3D images in a lossless manner, equally high-speed decompression of those images, and the ability to provide and render one or more lower resolution versions of the images before loading or receiving the entire compressed data set. Thus, use of this compression technique may result in faster network transfers and dramatically reduced time to first image when visualizing such compressed image data.

As discussed herein, the references to the following "progressive" compression technique generally refer to the scalability of resulting compressed image data, to generate multiple versions (e.g., resolutions) of chunks of a compressed image or image volume with sequential compression passes. In this fashion, the compression technique discussed herein is also quality progressive, as the image data may be successively compressed with lower quality at increasing levels of compression. However, the compressed image data produced with the disclosed progressive compression technique may still maintain a lossless property, as the image data is successively decompressed with higher quality at decreasing levels of compression—to ultimately recreate the original image.

In examples discussed herein, this image compression approach is implemented for use in medical imaging workflow settings. In a typical medical imaging workflow, the analysis of images and resulting diagnoses is frequently performed on a system that is physically separate from the modality where the images are acquired. The transfer of images from the modality to the analysis system (e.g., a workstation) may occur over a network with a push or pull model, but in either model, the time to complete such a transfer is dependent on network bandwidth and processing resources. With the techniques discussed herein, compression may be introduced into the medical imaging workflow in order to increase the effective bandwidth between network endpoints.

The technical benefits from this approach as applied to a 3D image set include: implementing the ability to preserve all detail from an original 3D image, meaning the compression technique is lossless; producing a significant (e.g., >2×) compression of the original 3D image data; utilizing a processor in an efficient fashion for compression operations; and, providing a progressive load capability to allow access to a reduced visual representation (e.g., lower-resolution) versions of the original 3D image from a subset of the compressed data. These techniques enable a useful increase in effective network/storage bandwidth, processing and memory usage, and in applicable settings, a corresponding reduction in time to transfer image data and render an initial image, particularly in a medical imaging viewing and visualization environment.

As discussed herein, the compression techniques are specifically adapted for use with processing circuitry commonly utilized in computing systems, including CPUs and microprocessors that utilize a single instruction multiple data (SIMD) architecture. The techniques discussed herein invoke specific SIMD commands in an x86 architecture for evaluating portions of the compressed data, allowing improved performance without necessarily having to increase processor clock rates or core counts. However, as will be readily understood, the compression techniques discussed herein may be scaled to higher levels of performance through the utilization of multiple processor cores and other forms of increased processor capabilities.

FIG. 1 illustrates a diagram of an example system configuration for implementing progressive lossless compression of medical imaging data according to an example described herein. Specifically, FIG. 1 illustrates an environment where imaging data is communicated from an image data source (modality 110), via a network (local area network 120), to an image data display location (workstation display system 128). It will be understood that FIG. 1 provides a simplified representation of a medical imaging environment, as the use of other complex image capture, processing, and display scenarios, networking equipment, and storage or archival systems may be involved in various medical diagnostic imaging and image analysis activities.

As shown in FIG. 1, imaging data 114 is captured by a modality 110, and transferred to a workstation display system 128, such as from a result of image analysis workflow operations. This imaging data 114, in various examples, may include two- or three-dimensional image data of a human subject, such as image data acquired from a medical imaging modality (e.g., an x-ray machine, computed tomography (CT) scanner, magnetic resonance imaging (MRI) machine, and the like). The imaging data 114 may be stored at a data store 112 at the modality or associated with the modality. For instance, the imaging data 114 may be directly or indirectly provided from a specialized medical imaging system such as a picture archiving communication system (PACS), vendor neural archive (VNA), or other image data retrieval, caching, or storage systems. The imaging data 114 may be viewed and represented at the modality system with use of a modality workstation 122 under the operation of a modality operator 124 (e.g., a radiology technician, nurse, or other skilled medical professional).

The imaging data 114 may be transferred to the workstation location, as part of a data push or pull in a medical imaging workflow, as discussed below. For example, a workstation display system 128 may be operated by a health practitioner 126 to perform a series of workflow operations on requested imaging data 114, with such workflow operations encompassing data visualizations that display, change, and interact with (e.g., augment, highlight, change, modify, remove, segment, etc.) features of the medical representations provided in the imaging data 114. For example, three-dimensional data visualizations may be generated and rendered as a representation of captured imaging data, for output in a graphical user interface of the workstation display system 128. The workstation display system 128 may provide output from a display device (e.g., monitor, screen, etc.) and receive input to the display device (e.g., via a keyboard, mouse, touchpad, touch screen, and the like), although other non-graphical forms of output and input may also be utilized.

The format of the imaging data 114 may be in a proprietary or industry standard format, such as in a Digital Imaging and Communications in Medicine (DICOM) format. This imaging data 114 may be further processed or consolidated by an image processing component (not shown) prior to processing and display in the operational workflow. For example, a series of two-dimensional medical images may be captured and combined into a set of three-dimensional medical images, within the imaging data 114. Many medical imaging modalities (e.g. MR, CT) produce multiple 2D images covering adjacent cross-sections within the human body. Multiple adjacent 2D images can be combined, then, into a single 3D image presented to the user as 3D imaging data. Among other reasons, this is performed in order to present a more complete and perceptible (3D) view of the anatomy being scanned.

The modality operator 124 or automated processes, algorithms, or models may operate to combine, filter, or extract portions of the imaging data 114, and store the imaging data 114 in the data store 112 for time-limited (e.g., temporary) or time-fixed storage. As further discussed below, a progressive compression technique 116 may also be applied upon the imaging data 114 at or after the modality location to facilitate the storage, transmission, and use of the imaging data 114.

In an example, series of data transfer operations are conducted via the network 120, and operate to transfer the imaging data 114 from the modality location to an image data display location. Such data transfer operations may include direct network communications to a workstation location, transfers via an intermediate system (e.g., a PACS, VNA), transfers to a workstation display system 128, or transfer to a workstation data store 118 available or accessible at the workstation location. It will be understood that, in many environments, the data transfer rates available within the modality location (e.g., between the modality 110 and the modality data store 112) and within the workstation location (e.g., between the workstation display system 128 and the workstation data store 118) are likely to exceed the data transfer rates available between the modality location and the workstation location via the network 120. Thus, the use of progressive compression technique 116 may assist the expedited transfer of data via the network 120.

In medical imaging viewing environments, a push or pull model is typically used to facilitate the timing and parameters for the transfer of imaging data. In a push model, the modality 110, upon completion of image acquisition and relevant reconstruction, proactively transfers the images from the modality location to the workstation location (e.g., in a DICOM format). The workstation location stores the received images on local persistent storage (e.g., in workstation data store 118). At some later point in time, the health practitioner 126 loads the images from the local storage into the relevant analysis software on the workstation display system 128. In contrast, in a pull model, the modality 110, upon completion of image acquisition and relevant reconstruction, stores the images on local persistent storage (e.g., in data store 112). At some later point in time, the health practitioner 126 requests and loads the images into the relevant analysis software on the workstation display system 128. Because the images are not yet present on at workstation location, they must be fetched from the modality location while the user waits. The use of progressive compression technique 116, applied to the imaging data 114, may provide benefits for transfers and storage of data in both push and pull models.

A key metric for evaluating the performance experienced by the health practitioner 126 in such an environment is the "time to first image". This time generally measures how much time elapses between when the user first requests the loading of images and when the user can begin his or her analysis. For applications visualizing 2D images exclusively, this time can be quite short and is primarily a function of network latency. For more advanced applications visualizing 3D images, however, the entire stack of images must typically be transferred before analysis can begin. As a result, the time to first image for advanced visualization workstations tends to be bandwidth-driven, rather than latency-driven. The pull model, in particular, is highly bandwidth sensitive because it does not hide any of the image transfer time via proactive transfers. Time to first image can be reduced by introducing improved networking and storage technologies. However, such solutions are expensive because they typically require dramatic overhauls of IT infrastructure and the associated capital costs. The approaches discussed herein may introduce a compression and decompression technique into the workflow in order to increase the effective bandwidth between endpoints.

In an example, compression operations introduced with the present techniques may be involved in one or multiple compression and data transfer approaches. A first approach, depicted in the medical imaging environment of FIG. 1 as on-the-fly compression 132, involves the application of compression technique 116 at the modality 110 or the modality data store 112. The on-the-fly compression 132 allows for the compression of image data on request, such as in response to a user request, a system or automated request, a scheduled event, or like operations that request a transfer of data from a first location to a second location. In further examples, the on-the-fly compression 132 may be performed according to scheduled, predicted, or controlled operations in a medical imaging diagnostic workflow (e.g., as a health practitioner 126 initiates a request to view images of a certain anatomical area), with on-the-fly decompression activities occurring at the workstation display system 128. In a second approach, depicted in the medical imaging environment of FIG. 1 as at-rest compressed storage 134, the application of the compression may be applied to store data in the workstation data store 118 in a compressed format, such as to increase storage capacity and data access times for the imaging data. In further examples, the at-rest compressed storage 134 may be performed according to scheduled, predicted, or controlled operations for data storage management (e.g., to archive data stored at the workstation location, upon occurrence or completion of a workflow event).

In the context of the environment depicted in FIG. 1, a workflow used to access and display images generally refers to a series of operations performed with some combination of manual (human-specified) and automated activity, to perform a task. One example of a workflow in the medical imaging field of use is a radiology read workflow, where a series of diagnostic images (e.g., produced by an imaging modality) are evaluated by a reviewing medical professional (e.g., a radiologist) to produce a diagnosis directly from the medical images. Another example of a workflow in the medical imaging field of use is an image review workflow, where captured medical images may be manipulated and evaluated by a clinician (e.g., a specialist, doctor, or other trained professional), such as to perform segmentation, quantification, or prediction of anatomical features of a medical image to confirm a diagnosis or observe the state of a particular medical condition. Other examples of workflows may involve other types of actions, feedback, and control that occur from interaction with a human user or users in a software application or accompanying computer system.

Although the environment of FIG. 1 is described in relation to medical image data processing, it will be understood that similar workflows and compressions involving other forms of medical data, and non-diagnostic or non-medical actions, may also be performed. Further, aspects of automated or computer-assisted medical imaging data compression may be applicable in both medically diagnostic and non-diagnostic (e.g., informational, educational, demonstrative, etc.) settings. Thus, although some of the examples herein refer to the processing of medical imaging data for diagnostic purposes (such as with radiology or pathology practices), the following techniques may be used with other types and forms of imaging data. Additionally, the compression and decompression techniques discussed herein may be modified with various forms of data processing, transfer, and display ordering, such as to prioritize the compression, transfer, or decompression of certain parts of a particular image view, image slab, image volume, or other collections of pixels, voxels, or other image data.

Figure 2:
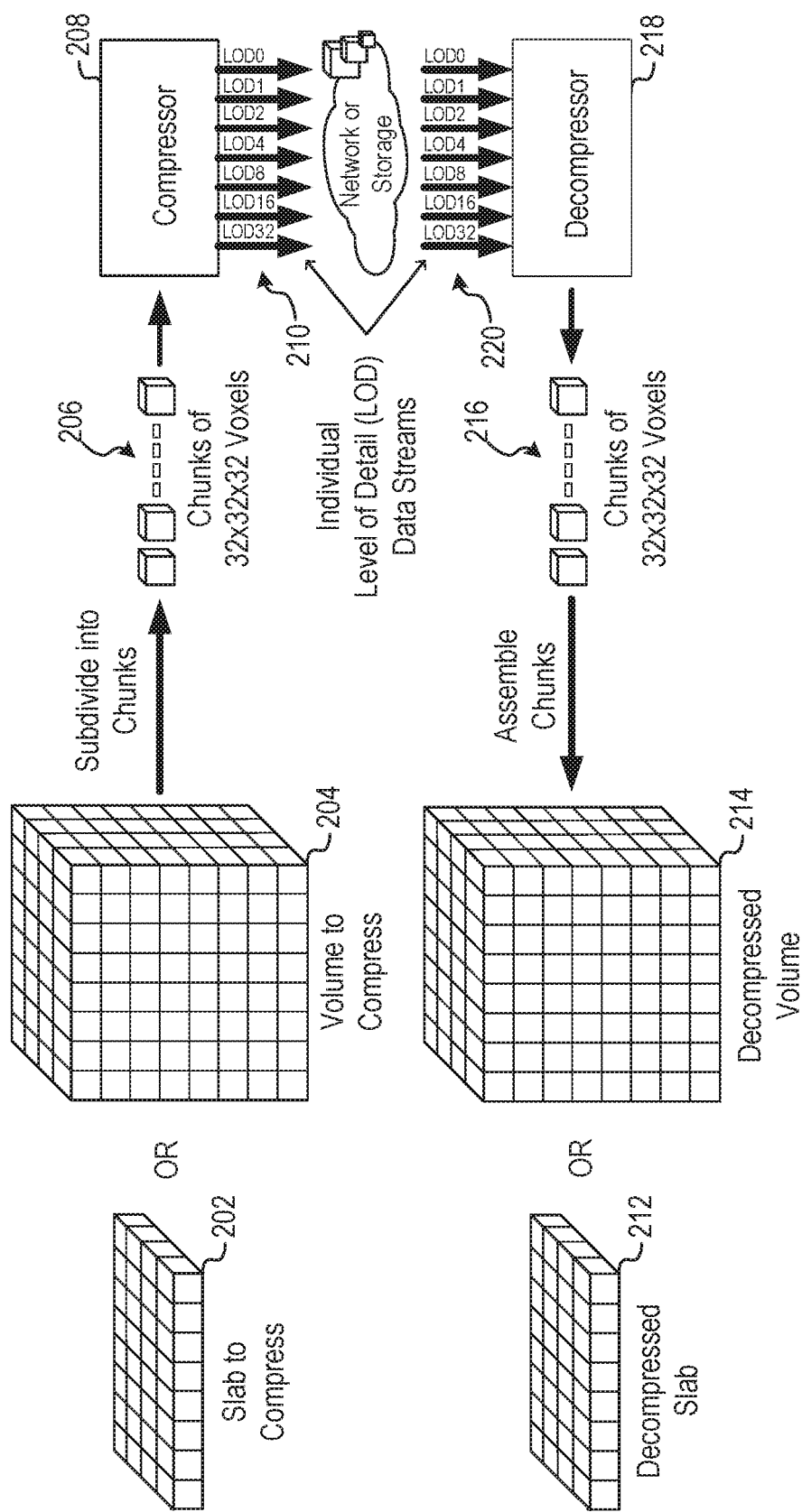
FIG. 2 illustrates an overview of image data distribution utilizing a progressive lossless compression technique, according to an example described herein.

FIG. 2 illustrates an overview of image data distribution utilizing a progressive lossless compression technique, according to an example described herein. In an example, the technique subdivides 3D medical images into chunks of voxels (e.g., cubes of 32×32×32 voxels) that are compressed or decompressed individually. This subdivision technique allows for an optimized and compressed distribution and storage of data, to the level of individual chunks of data. Further, this subdivision technique allows the distribution of data across multiple processor cores for compression operations as available and needed.

In an example, the input data is provided from a slab 202 of three-dimensional image data to compress, with the slab 202 including a particular portion or composition of 3D data. In another example, the input data is provided from a volume 204 of image data to compress, with such volume including multiple portions or compositions of 3D data. For instance, the volume 204 may provide a stacking of all (or most) of the acquired images, whereas the slab 202 may provide a smaller subset of the overall stacking of the acquired images. In further examples, all or a portion of the slab 202 or the volume 204 may be constructed from multiple images of a two-dimensional image or image set, such as a series of 2D images (e.g., CT images, MR images) generated from an imaging source (e.g., a medical imaging modality). As an example, a typical CT image may be produced at a resolution of 512×512 pixels. A slab produced may be constructed of 32 such images (when the chunk size is 32×32×32), and such that a slab may include 512×512×32 voxels. The number of images in a volume may be variable, and may range from the low hundreds to thousands (e.g., 2000+) or more of images depending on the scanning protocol employed. Thus, a typical CT volume may represent 512×512×640 voxels. However, it will be apparent that as use of increased scanning resolutions occurs, 2D images may be produced at even higher resolutions such as 1024× 1024 or 2048×2048 pixels, leading to an increased number of data in corresponding slabs or volumes.

As depicted in FIG. 2, the various chunks of data 206 (e.g., cubes of 32×32×32 voxels) are processed by a data compression technique, with compressor 208, to produce a progressive compression in respective level of detail (LOD) data streams 210. In an example, a LOD0 data stream may represent data from a basic compression of the original data, with no reduction in resolution (e.g., the LOD0 data stream includes data filtered at the original 32×32×32 voxel size, and this data stream captures how to reconstruct the original 32×32×32 image from the 32×32×32 filtered image); a LOD1 data stream may capture a 1× resolution compression (e.g., the LOD1 data stream includes data compressed and reduced to 16×16×16 voxel chunks, and this data stream captures how to reconstruct the filtered 32×32×32 image from the 16×16×16 subsampled image); a LOD2 data stream may capture a 2× resolution compression (e.g., the LOD2 data stream includes data compressed and reduced to 8×8×8 voxel chunks, and this data stream captures how to reconstruct the 16×16×16 subsampled image from the 8×8×8 subsampled image); a LOD4 data stream may capture a 4× resolution compression (e.g., the LOD4 data stream includes data compressed and reduced to 4×4×4 voxel chunks, and this data stream captures how to reconstruct the 8×8×8 subsampled image from the 4×4×4 subsampled image); a LOD8 data stream may capture a 8× reduced resolution (e.g., the LOD8 data stream includes data compressed and reduced to 2×2×2 voxel chunks, and this data stream captures how to reconstruct the 4×4×4 subsampled image from the 2×2×2 subsampled image); a LOD16 data stream may capture a 16× reduced resolution (e.g., the LOD16 data stream includes data compressed and reduced to a 1×1×1 voxel chunk, and this data stream captures how to reconstruct the 2×2×2 subsampled image from the 1×1×1 subsampled image voxel); and a LOD32 data stream may capture this smallest resolution (e.g., the 1×1×1 voxel chunk by itself). As will be apparent, other chunk sizes (e.g., 64×64×64, 128×128×128, N×N×N chunks of voxels, where N is a power of 2) and variations of LOD data streams may also be utilized with the compression and decompression technique discussed herein.

As discussed below with reference to FIG. 3, a respective LOD data stream may include a set of compressed voxels in addition to compressed voxel data (deltas) corresponding to the compression performed for the level of detail. The respective LOD data streams may be communicated via a network, maintained in storage, or processed by one or more data sources and data targets. Thus, as further shown in FIG. 2, the LOD data streams 220, provided from a source to a target, may be used to reconstruct images at a reduced level of compression (and an increased resolution), even to reconstruct the original data losslessly.

The various chunks of data (e.g., compressed cubes of 16×16×16 voxels) and the compressed voxel data (deltas) are processed by a data decompression technique, such as with decompressor 218, to produce a higher resolution of image data. For instance, the various chunks of data 216 are produced from the decompressor 218, and can be reconstructed into a decompressed volume 214 or a decompressed slab 212.

Figure 3:
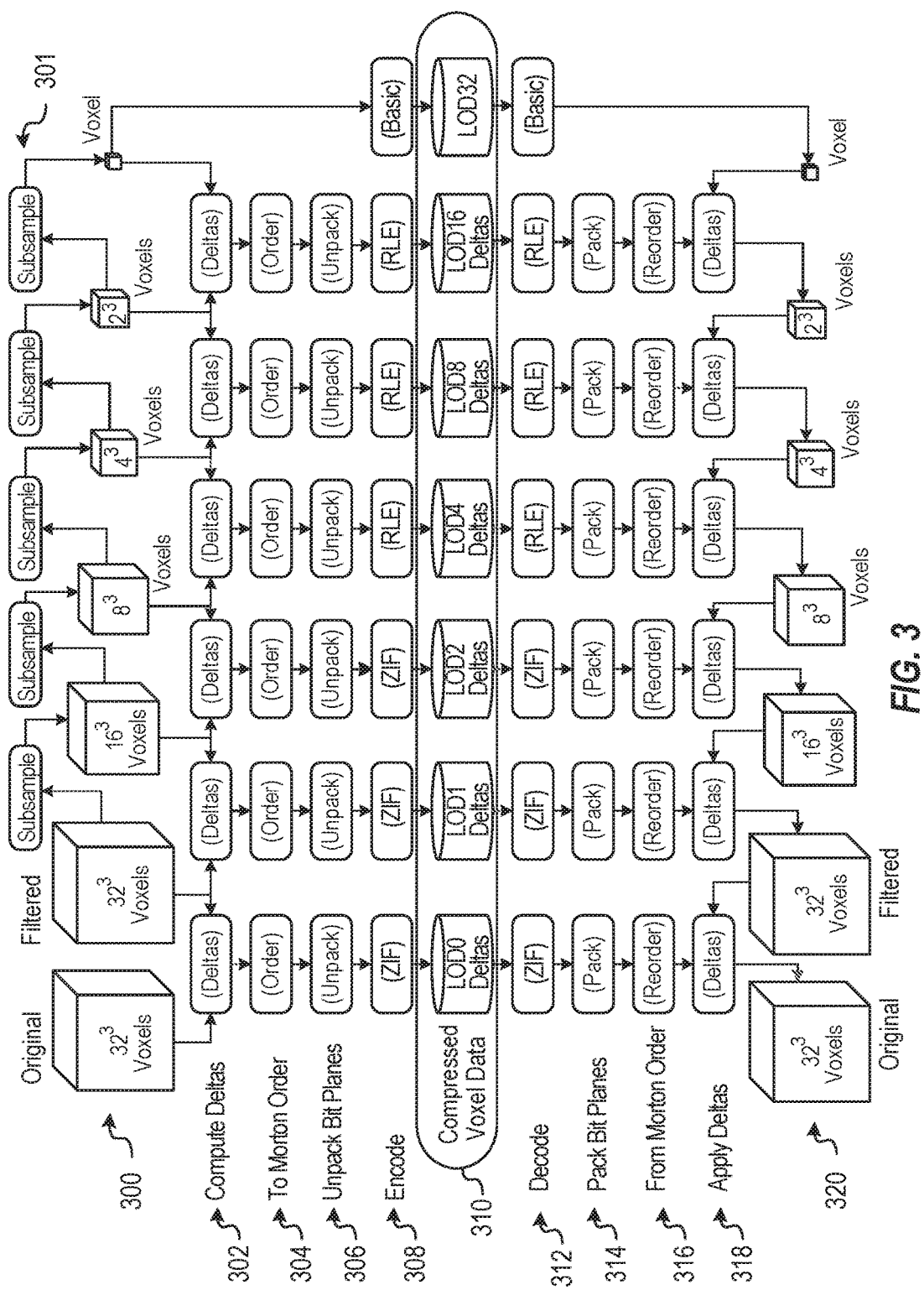
FIG. 3 illustrates a processing flow for generating versions of compressed voxel data with a progressive lossless compression technique, according to an example described herein.

FIG. 3 illustrates an example processing flow for generating versions of compressed voxel data, utilizing a progressive lossless compression technique. The processing flow in FIG. 3 specifically illustrates the creation of respective compressed voxel data sets, for distribution among different LOD data streams. As shown, this processing flow depicts the creation of both reduced image data (e.g., subsampled chunks of voxels 300) and compressed voxel data (e.g., optimized delta values from voxel data 310). The use of the compression technique allows for progressive compression at a plurality of levels in respective LODs. However, this compression technique also allows the re-creation of a prior level of compression, up to the original uncompressed data if available, thus presenting an opportunity for use in an imaging display environment as a lossless compression technique. Further, this progressive compression aspect provides the capability to decompress without requiring all of the information used to compress the original data.

As shown in FIG. 3, the chunks of voxels 300 are progressively reduced in resolution, and differences from the compression of each LOD are also computed and optimized into deltas as compressed voxel data 310. In an example, the progressive compression technique may include the sequential use of the following reduction and compression operations.

Subsampling (operation set 301): Down-samples a cube of voxels by computing the average over adjacent voxels (e.g., 2×2×2 neighborhoods of voxels). In an example, integer division is used, but with proper to-nearest rounding behavior. Other forms of sampling or resolution scaling may be utilized in addition or in place of the subsampling operations.

Compute Deltas (operation set 302): Computes the difference between voxels from two successive LODs. In an example, the differences not computed and stored using traditional two's complement binary arithmetic. Rather, as discussed below with reference to FIG. 4B, an alternate representation may be utilized that produces values with many leading zero bits for both positive and negative differences of small magnitude.

To Morton Order (operation set 304): Shuffles the difference values (in memory) of three-dimensional data from a traditional x-y-z order to a Morton order. Applying this shuffling step causes difference values that are located close to one another in the image itself to be located more closely in a memory representation. This, in turn, tends to lengthen the sequences of consecutive zero bytes produced by the following Unpack Bit Planes operations, thus improving the overall compression ratio.

Unpack Bit Planes (operation set 306): Extracts individual bit planes from the difference values, starting with the zeroth bit plane, and stores the bits adjacently in memory. Because voxels that are physically close to one another in the image tend to have similar values, the difference between such voxels versus a local average tends to be small in magnitude. Further, a non-two's-complement difference value representation employed by the Compute Deltas operation (operation 302) exploits a tendency to produce numerous zeros in the upper bits of the difference values. Thus, an unpack bit planes operation may concentrate those zero bits into consecutive zero bytes.

Encode (operation 308): Performs an encoding operation upon the reordered and unpacked delta values, to optimize a compression of the resulting delta representations. The encoding operations depicted in FIG. 3 for various LODs include the following:

Encode RLE (Run-Length Encoding): As discussed above, previous operations are designed to concentrate a chunk's information entropy near the beginning of the byte sequence produced by Unpack Bit Planes (operation 306), with the redundancy extracted as long sequences of consecutive zero bytes nearer the end of the byte sequence. Consequently, an extremely simple encoding can be employed to compress the data. In an example, encoding of deltas from certain voxel comparisons may be employed with a simplified RLE that encodes only runs of zero bytes. For example, the delta comparisons between 8×8×8 and 4×4×4 voxel cubes, 4×4×4 and 2×2×2 voxel cubes, and 2×2×2 and 1×1×1 voxel cubes, may be processed with RLE.

Encode ZIF (Zeros In Frames): For larger LODs, extremely long sequences of consecutive zero bytes are likely to be generated. These longer runs of zero bytes may be compressed using an additional encoding that can be implemented even faster than the Encode RLE step. For example, the delta comparisons between 16×16×16 and 8×8×8 voxel cubes, 32×32×32 and 16×16×16 voxel cubes, and 32×32×32 (unfiltered/original) and 32×32×32 (filtered/modified) voxel cubes, may be processed with ZIF encoding.

Encode Basic: As depicted in FIG. 3, the LOD32 data stream includes a single voxel (1×1×1) containing an average value for all 32,768 voxels in the original 32×32×32 chunk. This single voxel value may simply be stored as-is.

A set of optimized and compressed voxel data 310 is produced from the sequential operations 304, 306, 308, in the form of deltas (a delta data set) at a particular level of detail. This optimized delta data set, in combination with a set of reduced-resolution voxels, may be used to recreate a higher resolution of the voxels. For instance, when starting with 32×32×32 voxel chunks as the original data size, a 16×16×16 voxel chunk in combination with the optimized deltas (reflecting the differences between 32×32×32 and 16×16×16 data) can be decompressed into a 32×32×32 voxel chunk. In an example, decompression operations may be performed with the following individual steps:

Decoding (operation 312): Applies a decoding approach to expand the encoded, optimized delta data set (produced from encoding operation 308). For instance, Decode ZIF is an inverse function of Encode ZIF that expands the encoded lengths of zero bytes; Decode RLE is an inverse function of Encode RLE that expands the encoded lengths of zero bytes; and Decode Basic is an inverse function of Encode Basic that extracts the single LOD32 voxel value.

Pack Bit Planes (operation 314): The inverse function of Unpack Bit Planes. This function reconstructs the original difference values from the previously-separated (unpacked) bit planes.

From Morton Order (operation 316): The inverse function of To Morton Order. This function returns the difference values (in memory) for the 3D voxel chunks from Morton order to traditional XYZ order.

Apply Deltas (operation 318): The inverse function of Compute Deltas. This function applies the non-two's-complement difference values to the voxel values in the prior LOD, producing the next higher LOD. As a result of the decompression function, decompressed chunks of voxels 320 may be produced that are identical to the pre-compressed chunks of voxels 300.

Figure 4A:
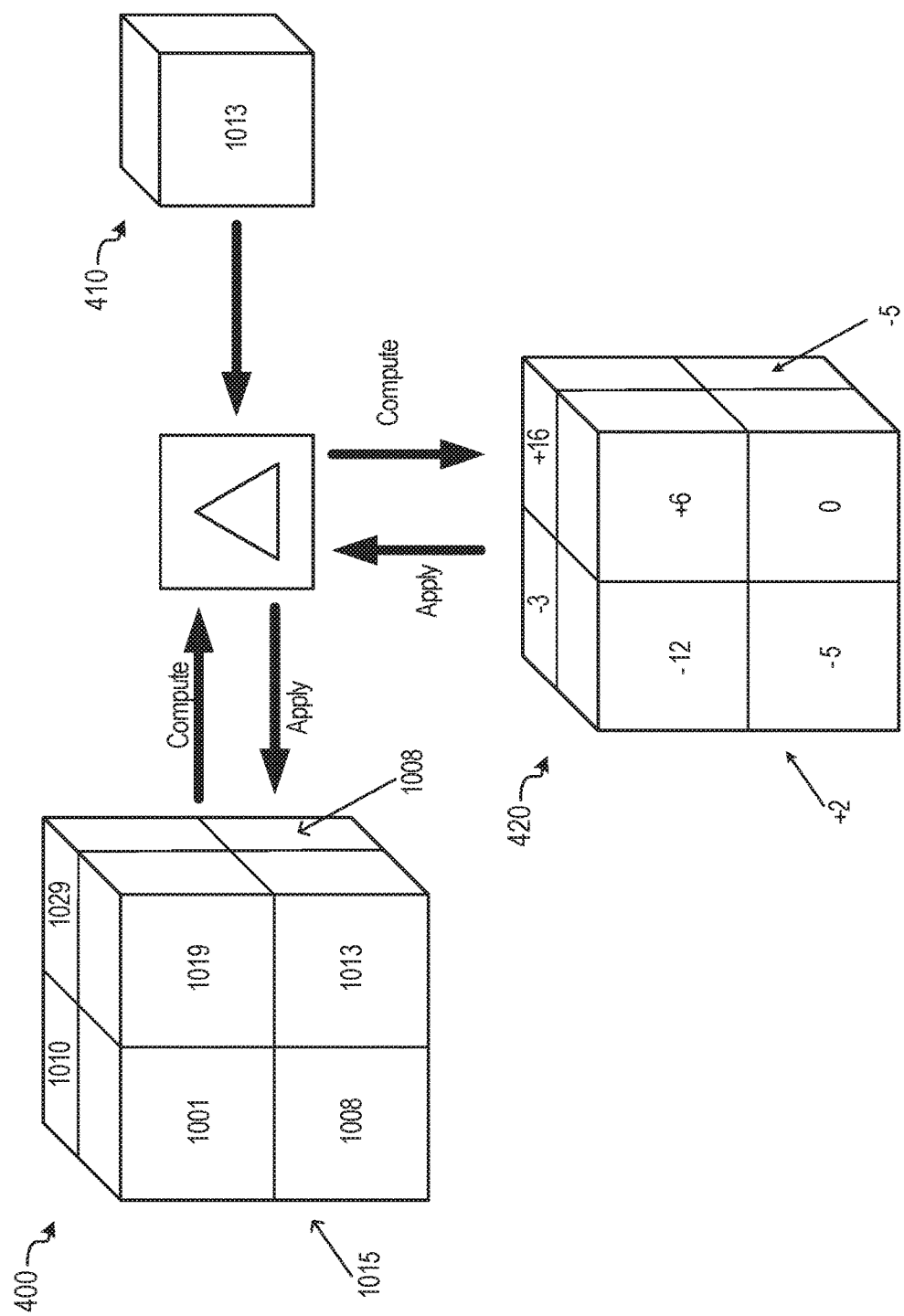
FIGS. 4A and 4B illustrate a technique for generating a delta representation between versions of compressed voxel data, according to an example described herein.
Figure 4B:
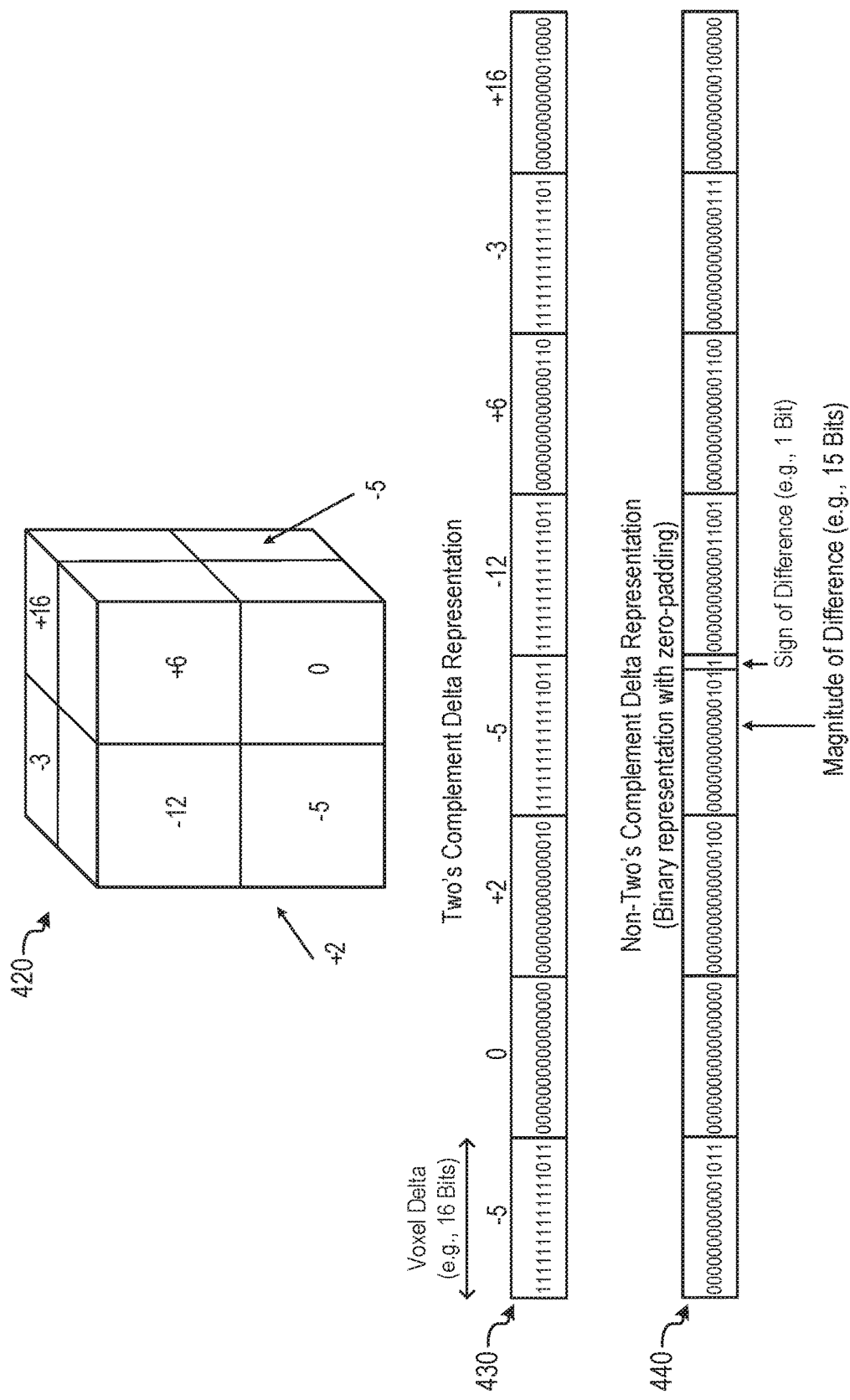

FIGS. 4A and 4B illustrates an example technique for generating a delta representation between versions of compressed voxel data. As shown, a 2×2×2 cube of voxels 420 indicates various delta values resulting from subsampling a larger resolution of data into a smaller resolution of data. This cube of voxels 420 specifically represents the deltas between a 2×2×2 cube of voxels at LOD(n) (cube of voxels 400) and a corresponding single average voxel in LOD(2n) (voxel 410). The delta values, as shown, are represented by integers (negative or positive whole numbers).

A conventional two's-complement binary representation of these delta values is shown in representation 430. Notably, a two's-complement binary representation of various negative and positive numbers results in a mix of negative numbers with leading ones, and positive numbers with leading zeros. In an example, the Compute Deltas and Apply Deltas compression operations (e.g., operations 302, 318) utilize a non-two's-complement delta representation 440 that causes both positive and negative small delta values to be represented with a large number of leading zeros. This arrangement, in turn, allows simpler back-end encodings to be used, improving the overall performance (speed) of the compression technique.

Specifically, as shown, the non-two's-complement delta representation 440 of the delta values for the cube of voxels 420, is provided with a binary representation of an absolute value of an integer, and an indication of a sign, for each respective numeric delta value. Further, the indication of the sign of the respective numeric delta value is included in a least significant bit. Use of this representation for a respective numeric delta value allows each of the represented delta values to typically be padded with many leading zeros, which in turn allows increased compression of delta data.

Figure 5:
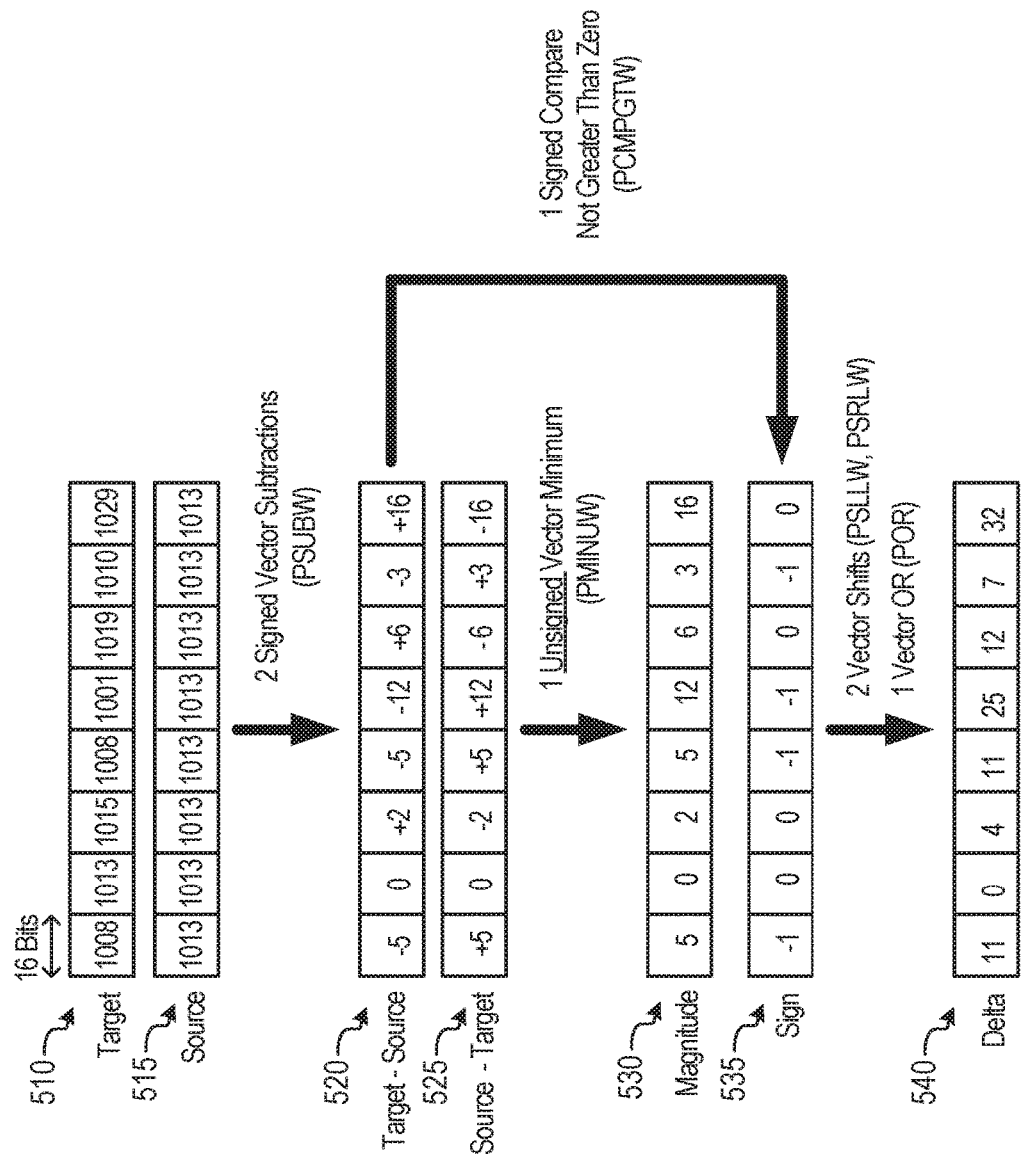
FIG. 5 illustrates a further technique for generating a delta representation between versions of compressed voxel data within a processing architecture, according to an example described herein.

FIG. 5 illustrates a further technique for generating a delta representation between versions of compressed voxel data within a processing architecture, according to an example described herein. In an example, the compression operations may be adapted to efficiently utilize instructions from the SIMD architecture found in modern computer microprocessors, leading to higher performance optimizations of the compression technique. For instance, FIG. 5 illustrates an optimized computation that may be performed on the non-two's complement data representation described above and depicted in FIG. 4B.

As a specific example, FIG. 5 illustrates a sequence of operations that can be used to compute a non-two's complement data representation for 8 voxels using only 7 instructions, such as in an implementation of the Compute Deltas operations (operation 302) on an SSE instruction set provided in x86 architectures. As shown, in an example where respective data values are provided from a target data representation 510 and a source data representation 515, two operations for signed vector subtractions are performed with the PSUBW instruction, to compute respective deltas, to produce two sets of data differences 520, 525. Further, the operation of one unsigned vector minimum operation with the PMINUW instruction may produce a set of magnitude values 530. These magnitude values 530 may be accompanied by respective sign values 535 (−1 or 0) produced with one signed compare not greater than zero operation, to produce sign values with the PCMPGTW instructions.

Finally, delta values 540 are produced from two vector shift operations (e.g., with PSLLW and PSRLW instructions) and one vector OR (e.g., with a POR instruction). The resulting delta values 540 may be further provided in a non-two's complement data representation (e.g., with the data representation described above with reference to FIG. 4B), ordered (e.g., with a Morton order), unpacked, and encoded (e.g., with the encoding described below with reference to FIGS. 6A-6B), for further optimization and compression.

Figure 6A:
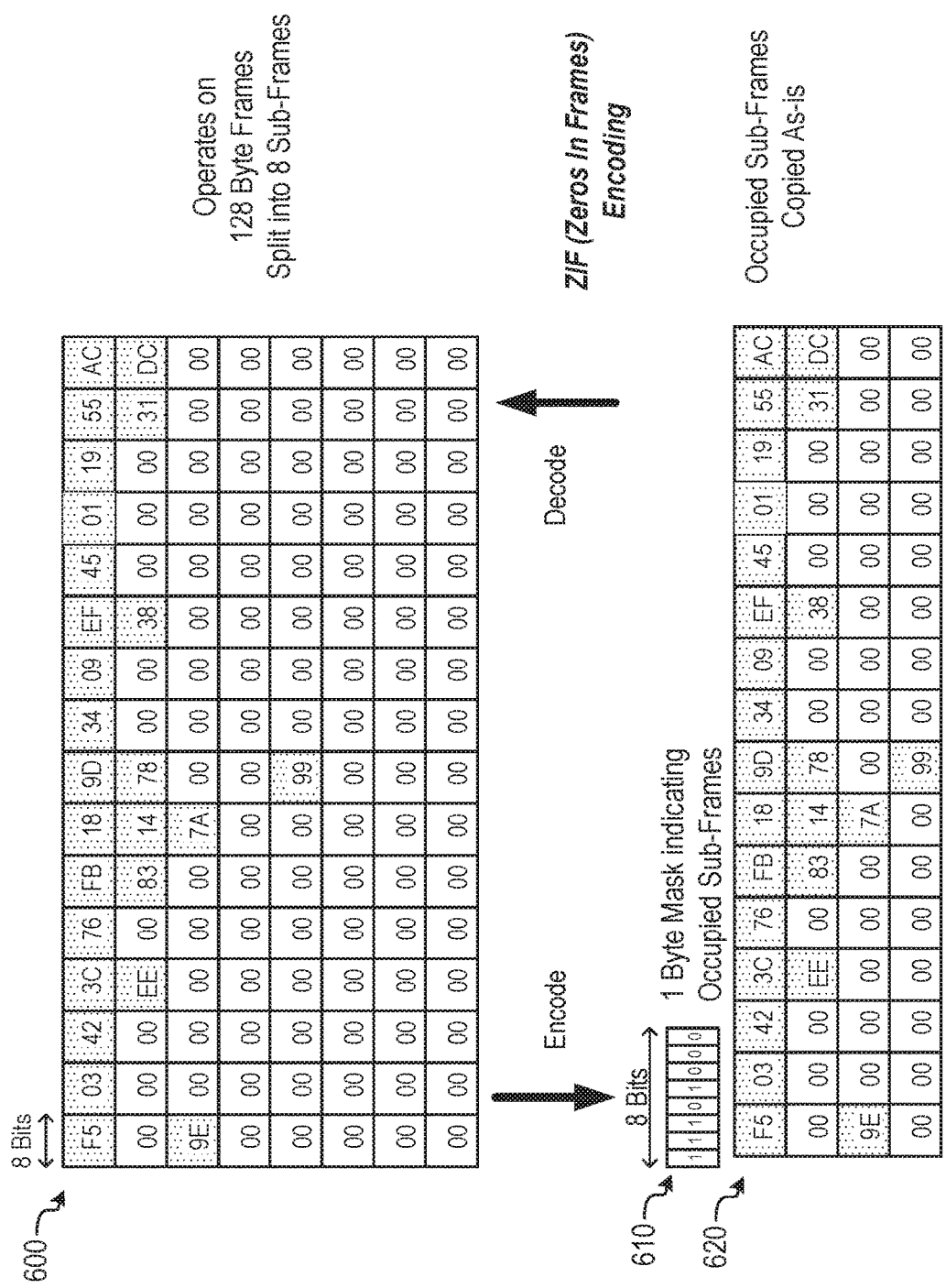
FIGS. 6A and 6B illustrate a technique for performing zeros-in-frames encoding on compressed voxel data, according to an example described herein.
Figure 6B:
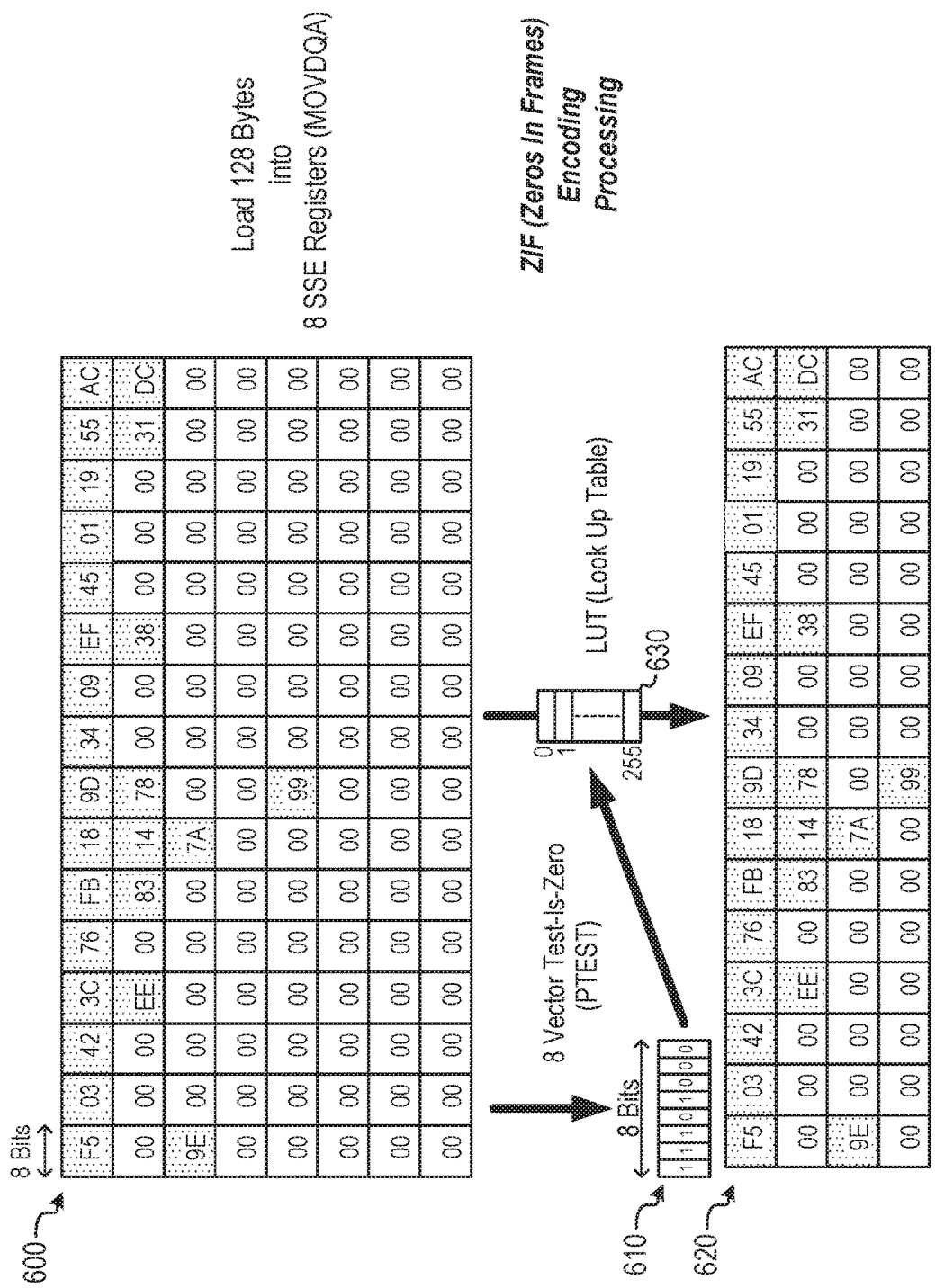

FIGS. 6A and 6B illustrate a technique for encoding a version of compressed voxel data, according to an example described herein. As discussed above, the Encode ZIF and Decode ZIF operations (e.g., operations 308, 312) utilize an encoding that exploits the previous step's ability to transform the repetitiveness of 3D medical images as zero bytes in order to quickly produce a useful compression ratio.

In the example depicted in FIG. 6A, ZIF encoding provides an encoding scheme for the reduction of empty (zero) data as follows. The data to be encoded is first split into 128 Byte frames (e.g., frame set 600). Each 128 Byte frame is then encoded with: 1) A single byte (mask 610) whose individual bits correspond to the respective the sub-frames (e.g., 8 subframes) within the frame, to provide a value of 0 when that subframe contains all zero bytes, or a value of 1 when that subframe contains non-zero bytes; and 2) The entire 16 Byte content of a respective subframe that contains a non-zero byte (frame set 620), which is maintained in its original order. (This is performed on the subframes that have non-zero bytes).

This ZIF encoding operation compactly represents long sequences of zero bytes, while also having the advantage of being easy to implement using vectorized operations, and requiring fewer data-dependent conditionals than RLE encoding. In a further example, the ZIF encoder can optionally be provided with a mask indicating which bit planes are occupied, which is then used to only encode the non-empty bit planes—improving performance further, and increasing the compression ratio.

FIG. 6B further illustrates ZIF encoding operations performed to identify the four subframes that include zeros exclusively. In an example, all of the bytes of frame set 600 are loaded into respective registers, such as eight Streaming SIMD Extensions (SSE) registers. The MOVDQA instruction is used to load 16 single-byte values from memory into a SSE register, shown in FIG. 6B with 128 bytes total in eight SSE registers. In FIG. 6B, Eight Vector Test-is-Zero (PTEST) instructions are also shown as being utilized. The PTEST instruction returns a value of 1 if all of the 16 single-byte values in a SSE register are zero, or a value of 0 otherwise. This instruction is used 8 times, once to each of the SSE registers in 600, to produce the 8-bit mask 610. The 8-bit mask 610 is used as an index into a look-up-table (LUT) 630 that includes 256 entries. Each entry in the LUT is a 64-bit value that informs the encoder/decoder of which SSE registers contain non-zero sub-frames.

Although the examples discussed above were provided in relation to 3D imaging data, it will be understood that the compression and decompression techniques may also be applied within volumes or sets of 2D imaging data. Specifically, the utilization of subsampling (operation 301), computing deltas (operation 302), unpacking bit planes (operation 306), and encoding (operation 308) may be used to generate progressively compressed 2D image data and optimized 2D image data deltas. Further, the concepts discussed above for decompression (operations 312, 316, 318) and LOD streams (streams 210, 220), and the SIMD instructions optimizations available for delta encodings, also may be applicable for 2D image compression. For example, in a subsampling technique, an average of 4 (2×2) voxels instead of 8 (3×3×3) voxels may be utilized. Thus, the sub-steps of the compression and decompression techniques discussed above for 3D image data compression are also applicable for 2D image data compression, just with the omission of operations on the third dimension.

Figure 7:
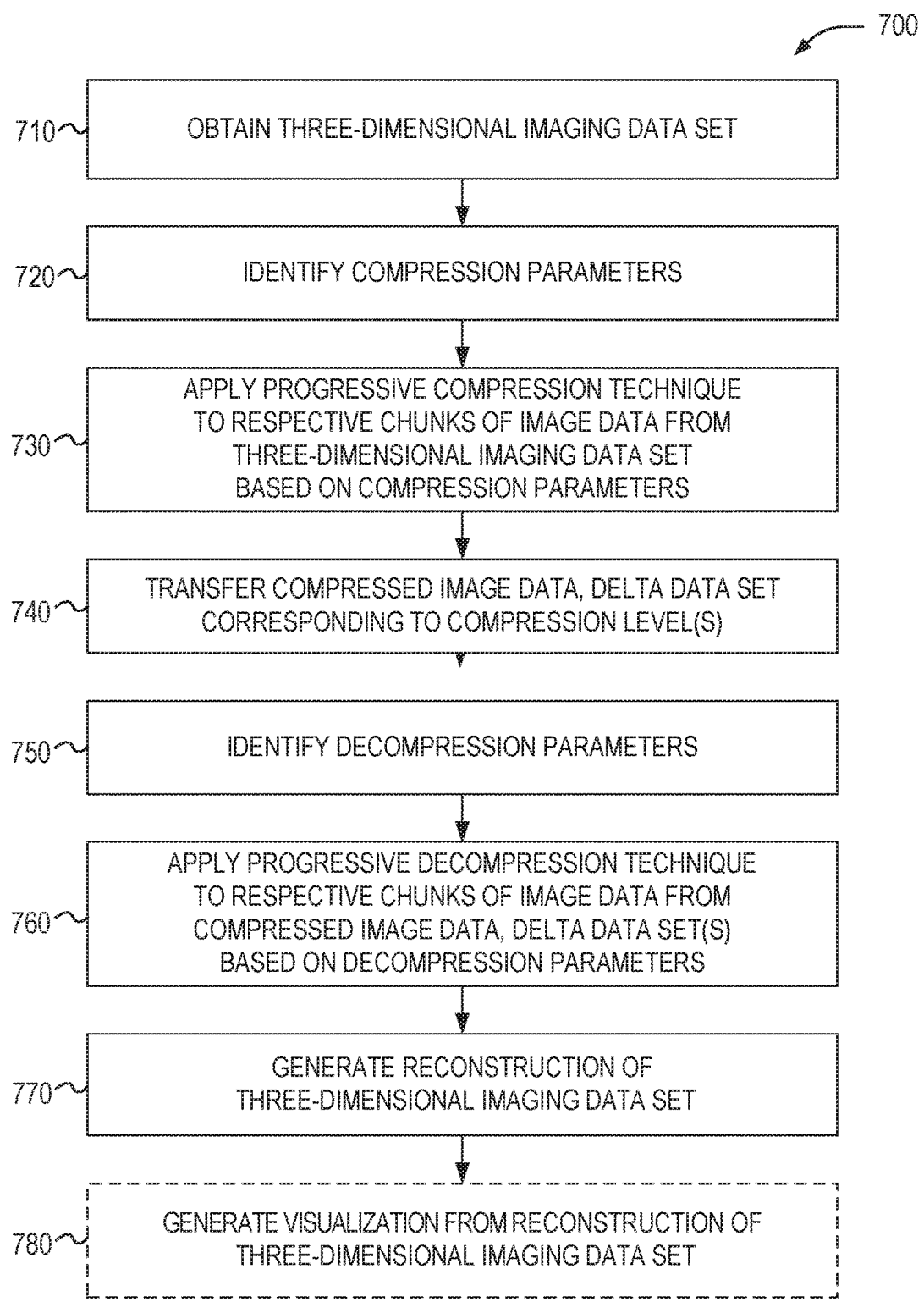
FIG. 7 illustrates a flowchart of a method performed in an image processing environment for compressing, transferring, and decompressing data, according to an example described herein.

FIG. 7 illustrates a flowchart of an example method performed in an image processing environment for compressing, transferring, and decompressing data. As shown, the flowchart 700 depicts a set of sequential operations to effect compression, transfer, and decompression of imaging data (e.g., for 3D imaging data in a medical imaging environment). It will be understood that the summary of activities portrayed in FIG. 7 is provided for purposes of illustration, and that many more detailed activities (including activities provided in another order or sequence) suggested herein may occur among various computing systems and processing components. Further, as will be apparent, the various compression and data use operations described above with reference to FIGS. 1 to 6B may be integrated among the following operations.

The flowchart 700 initially depicts an operation for obtaining a three-dimensional imaging data set (operation 710), such as the access, request, identification, retrieval, or parsing of 3D image data (e.g., a 3D slab or data volume produced from a medical imaging modality). The flowchart 700 continues with the identification of compression parameters (operation 720) such as a level and type of compression, a desired level of detail, an order that LOD streams are transmitted, and other conditions relating to use of the compression technique. In an example, the compression technique is performed to compress data down to the lowest level of detail (e.g. LOD32, the highest compression available).

With the imaging data set and the compression parameters, a compression component (e.g., a configured computing system) operates to apply a progressive compression technique to respective chunks of image data (operation 730). This progressive compression technique is performed on the 3D image data, based on the compression parameters, to iteratively compress the imaging data to a LOD. In an example, the progressive compression technique may utilize the operations described above with reference to FIGS. 2 and 3, including the production of respective LOD streams. For instance, a respective LOD stream may provide a reduced-resolution set of data (e.g., subsampled to a particular resolution) in addition to a delta data set (e.g., compressed and optimized delta data) that can be used to re-create a higher resolution set of data.

The flowchart 700 continues with the transfer of compressed image data (operation 740), such as over a network with on-the-fly or storage-based compression. Further operations in the flowchart 700 continue in connection with image decompression and use operations.

The flowchart 700 further continues with the identification of decompression parameters (operation 750) such as a level and type of decompression, a desired level of detail to decompress to, and other conditions relating to use of the decompression technique. In an example, the identification of the decompression parameters includes a specification of lossless data quality, to return to the original image data state. The decompression technique then operates to apply a progressive decompression of the respective chunks of the 3D image data (operation 760). This progressive decompression is performed on the 3D image data, based on the compression parameters, to iteratively decompress and expand image data chunks as indicated by the respective delta values. From this progressive decompression, a reconstruction of the three-dimensional imaging data set may be created (operation 770). Finally, the operations of the flowchart 700 may conclude with the use of the decompressed imaging data, such as the generation of a visualization from a reconstruction of the 3D image data (operation 780). In a further example, the decompressed data may be progressively loaded and represented (e.g., from a lower resolution) and ultimately replaced by the lossless data.

Figure 8:
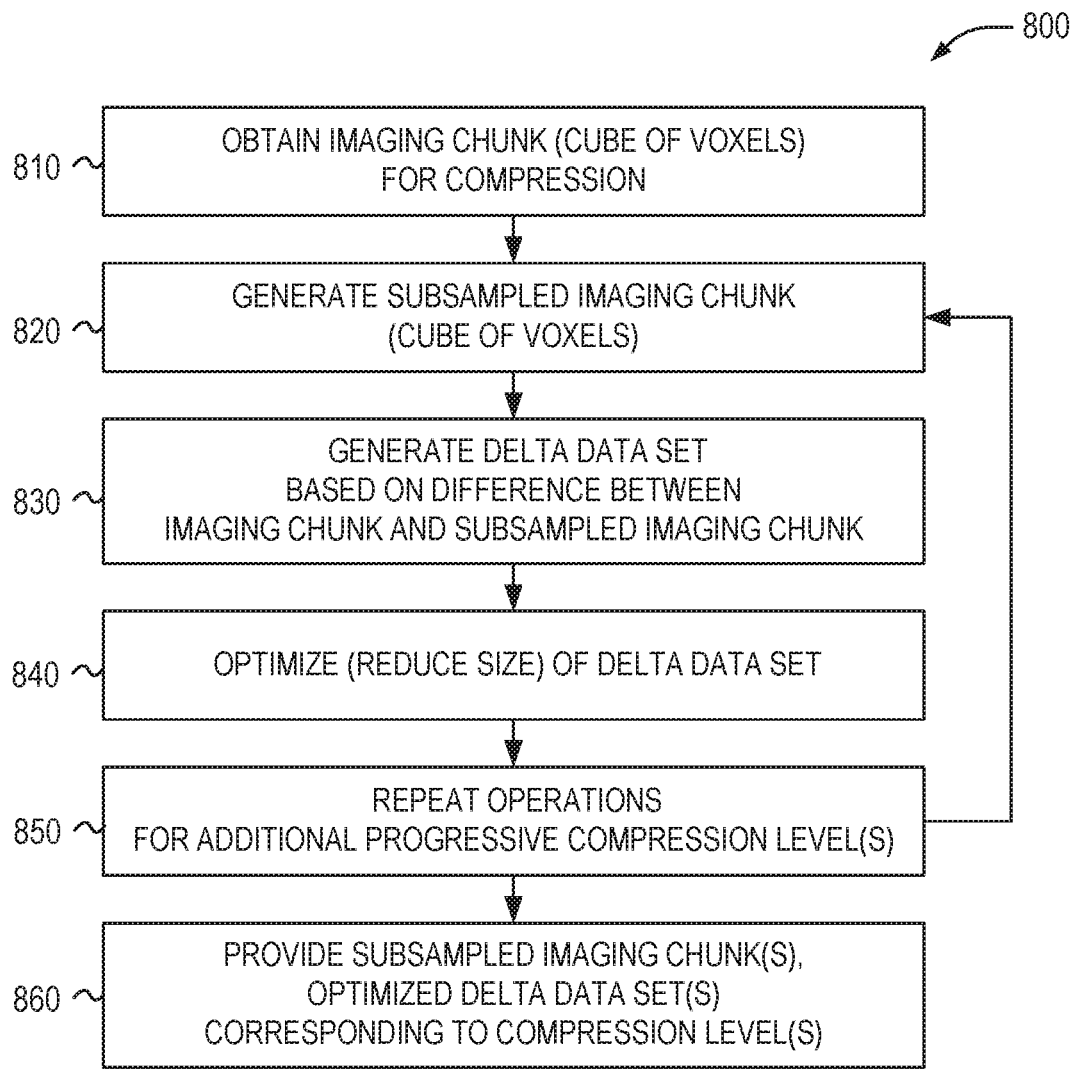
FIG. 8 illustrates a flowchart of a method performed by a computing system for compression of three-dimensional image data, according to an example described herein.

FIG. 8 illustrates a flowchart of an example method performed by a computing system for compression of three-dimensional image data. This flowchart 800 provides a depiction of operations used to apply a compression technique (such as the progressive compression technique referenced in operation 730), but it will be understood that additional operations, including the integration of the operations from flowchart 700 of FIG. 7 and other compression operations referenced above of FIGS. 3-6B, may be optionally implemented into the depicted flow.

The operations depicted in the flowchart 800 include obtaining a cube of voxels from a three-dimensional image data set (operation 810), and performing a compression technique on the cube of voxels (operations 820-840). In an example, the compression technique includes generating a subsampled (reduced resolution) cube of voxels from the cube of voxels (operation 820), and generating a delta data set from the subsampled cube of voxels (operation 830). In an example, the delta data set is generated to indicate the differences between voxels in the cube of voxels and the subsampled cube of voxels. Also in an example, the subsampled cube of voxels is generated from downsampling the cube of voxels by computing an average value of a plurality of voxels adjacent to the cube of voxels.

The operations of the flowchart 800 continue with operations to optimize the size of the delta data set (operation 840). For example, the delta data set may include data for a plurality of numeric delta values that indicate the differences between voxels in the cube of voxels and the subsampled cube of voxels. In an example, the plurality of numeric delta values may be represented in the delta data set, for respective numeric delta values, with a non-two's-complement delta representation. In a further example, the non-two's-complement delta representation provides a binary representation of an absolute value of an integer for a respective numeric delta value and an indication of a sign of the respective numeric delta value. For instance, the indication of the sign of the respective numeric delta value may be included in a least significant bit of the binary representation, for each of the respective numeric delta values, such that the most significant bits of the binary representation are typically padded with at least one zero. In still a further example, the compression technique performed on the cube of voxels further may include arranging respective delta values generated from the subsampled cube of voxels in a Morton order, unpacking bit planes of the arranged respective deltas values, and performing an encoding on the unpacked bit planes. For instance, the encoding may be performed with use of a zeros-in-frames (ZIF) encoding technique to identify frame locations of zero bytes, or a run-length encoding (RLE) technique to encode runs of zero bytes.

Further operations may be performed to continue the compression operations for one or more additional progressive compression levels (operation 850). This may be implemented by repeating the operations of generating a further subsampled cube of voxels and generating a further delta data set, to produce progressively compressed cubes of voxels and progressively compressed delta data sets from successively subsampled cubes of voxels. In a specific example (illustrated in FIG. 3), the original cube of voxels is a 32×32×32 set of voxels, the first subsampled cube of voxels is a 16×16×16 set of voxels, and the progressive compression techniques further produce a 8×8×8 set of voxels, a 4×4×4 set of voxels, a 2×2×2 set of voxels, and a single voxel, from the cube of voxels, and the first delta data set is produced from differences between the 32×32×32 set of voxels and the 16×16×16 set of voxels, and the subsequent delta data sets are respectively produced from differences between the 16×16×16 set of voxels and the 8×8×8 set of voxels, between the 8×8×8 set of voxels and the 4×4×4 set of voxels, between the 4×4×4 set of voxels and the 2×2×2 set of voxels, and between the 2×2×2 set of voxels and a single voxel. In still a further example, the original cube of 32×32×32 voxels is subjected to an initial filtering or processing technique and used to produce a filtered or processed cube of 32×32×32 voxels.

The operations of the flowchart 800 conclude with providing the subsampled cube of voxels and the delta data set (operation 860), such that the subsampled cube of voxels and the delta data set is operable with a decompression technique to losslessly recreate the cube of voxels. For instance, the various subsampled imaging chunks and optimized delta data sets, corresponding to a desired compression level (and LOD) may be transmitted.

Figure 9:
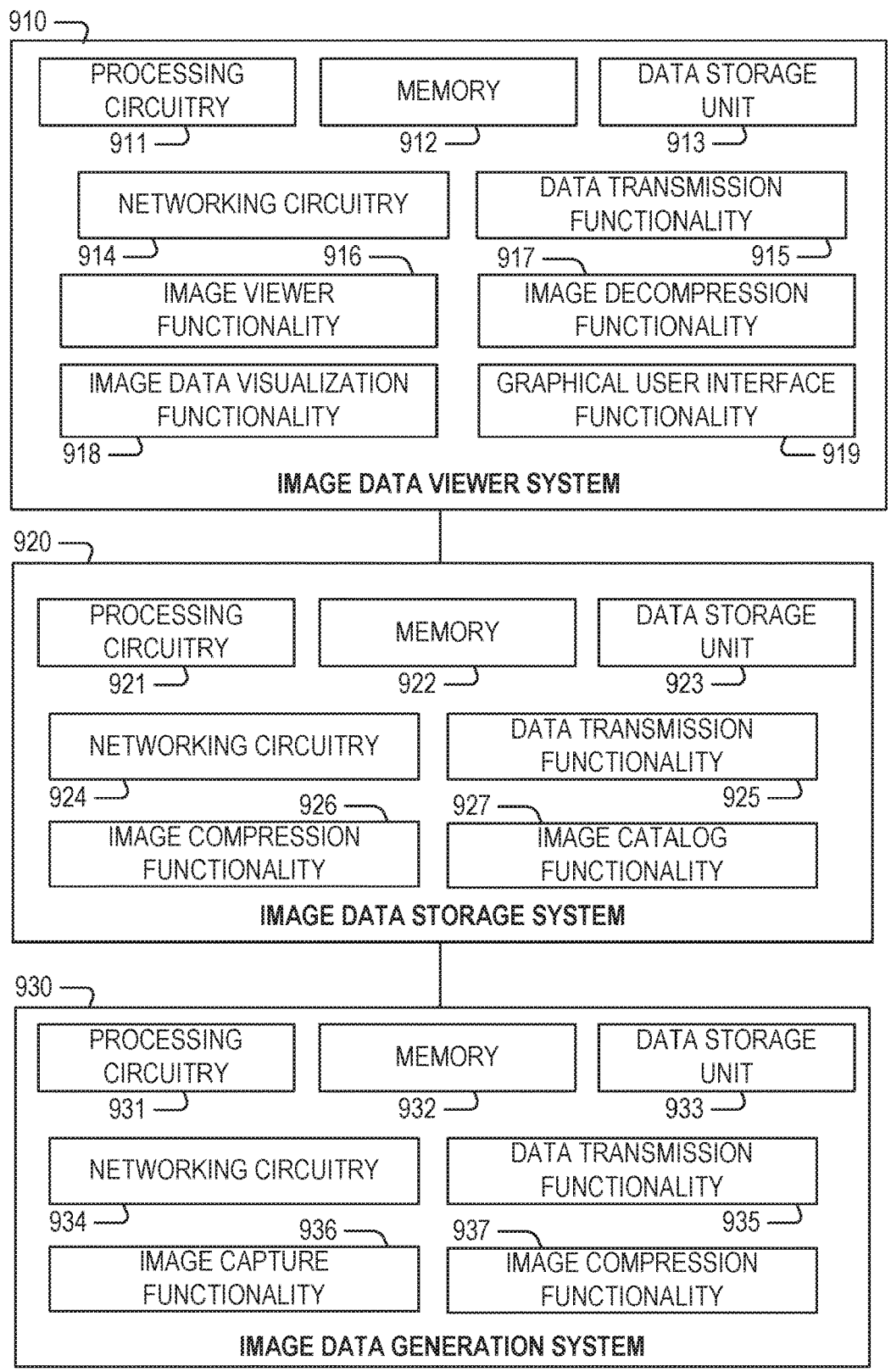
FIG. 9 illustrates a block diagram of systems and components in an image processing environment adapted for implementing progressive lossless compression, according to an example described herein.

FIG. 9 illustrates a block diagram of components in an example system used for capturing, processing, and viewing image data with the compression techniques described herein. For example, the system may include: an image data viewer system 910 (e.g., a client system) configured to implement data viewing and visualization operations on compressed data using the techniques described herein; an image data storage system 920 (a centralized system) configured to store, host, and serve compressed image data using the techniques described herein; and an image data generation system 930 configured to generate and serve original image data and compressed image data using the techniques described herein. The following configuration specifically encompasses the image data storage system 920 configured to perform image compression, with compressed image data being transferred to the image data viewer system 910, followed by the image data viewer system 910 performing image decompression and output of a representation of the image data. However, the following configuration also encompasses the image data generation system 930 providing aspects of image compression and transmission.

For instance, in the context of a medical imaging processing environment, the image data generation system 930 may represent an imaging system (e.g., a medical imaging modality) used to capture image data; the image data storage system 920 may represent an intermediate image processing system (e.g., a picture archiving communications system (PACS), a vendor neutral archive (VNA), etc.) used to host a full, uncompressed version of the medical imaging data; and the image data viewer system 910 may represent an image viewing system (e.g., a imaging workstation) used to display the medical imaging data to an end user (e.g., a medical professional). The compression techniques may involve on-the-fly compression for data transfers between the image data viewer system 910 and the image data storage system 920 or the image data generation system 930. As referenced throughout this disclosure, the configuration and use of compression in a medical imaging environment may include the various forms of 2D and 3D data, regardless of the medical content of such images. Thus, it will be understood that the configuration depicted in FIG. 9 is applicable to other types of data distribution workflows and data processing scenarios beyond medical settings.

The image data viewer system 910, the image data storage system 920, and the image data generation system 930 may include respective hardware components, such as processing circuitry 911, 921, 931 to execute instructions, memory 912, 922, 932 used with the processing circuitry to execute instructions and provide data, data storage 913, 923, 933 to host and store instructions and data, networking circuitry 914, 924, 934 to communicate data among systems via a network, and data transmission functionality 915, 925, 935 to receive and transmit data (including uncompressed or compressed data) with use of the networking circuitry. The hardware components may operate with use of further hardware and software-implemented components (not depicted) located among the systems 910, 920, 930 for user input, output, and processing, such as aspects of a graphical user interface, output devices (such as to provide output of the graphical user interface) and input devices (such as to provide input for processing and actions in the graphical user interface).

The image data viewer system 910 may include components (e.g., programmed or specially arranged circuitry) for implementing image viewing and visualization features, such as through: image viewer functionality 916 that implements and executes image rendering and output on various portions of the imaging data (e.g., to generate a customizable view of the image data); image decompression functionality 917 that executes decompression operations on compressed image data; image data visualization functionality 918 that implements and executes visualization operations on various aspects of the imaging data (e.g., to visualize or enhance certain anatomical features or medical conditions); and graphical user interface functionality 919 to receive control input and output graphical representations of image viewer, image visualizations, and like representations or features. In a further example, an output device, and an input device (not depicted) are used to engage the graphical user interface functionality 919 with use of the processing circuitry 911 and memory 912 to implement features of the image viewer, image decompression, or image data visualization functionality.

The image data storage system 920 may also include image compression functionality 926 and image catalog functionality 927. In an example, the image compression functionality 926 is adapted to perform compression of the image data prior to transmission to the image data viewer system 910; and the image catalog functionality 927 is adapted to maintain a catalog, index, or library of image data among various image data views, such as for retrieval, searching, or access purposes. In this fashion, the image data storage system 920 may operate as a server, to receive data generated by the image data generation system 930, and to serve compressed data over a network to the image data viewer system 910.

The image data generation system 930 may also include image capture functionality 936 and image compression functionality 937. In an example, the image capture functionality 936 operates with use of imaging techniques (e.g., scanning, observing, monitoring, capturing) to obtain and generate image data from an object (e.g., a person, an animal, a plant, or even a non-living thing). The image compression functionality 937 may be used to generate a compressed version of the captured image data to be communicated the image data storage system 920 (e.g., with storage-based compression approaches) or to the image data viewer system 910 (e.g., with on-the-fly compression approaches).

In an example, the features of the image data storage system 920 and the image data generation system 930 may be integrated or combined into a single system. In other examples, the features of the image data storage system 920 and the image data generation system 930 may be distributed among multiple computing machines, and the image data viewer system may obtain compressed image data that is process among such multiple computing machines. Other variations to implement push and pull approaches to imaging data and on-the-fly or at-rest image data compression may cause changes to the hardware provided within the systems 910, 920, 930.

Figure 10:
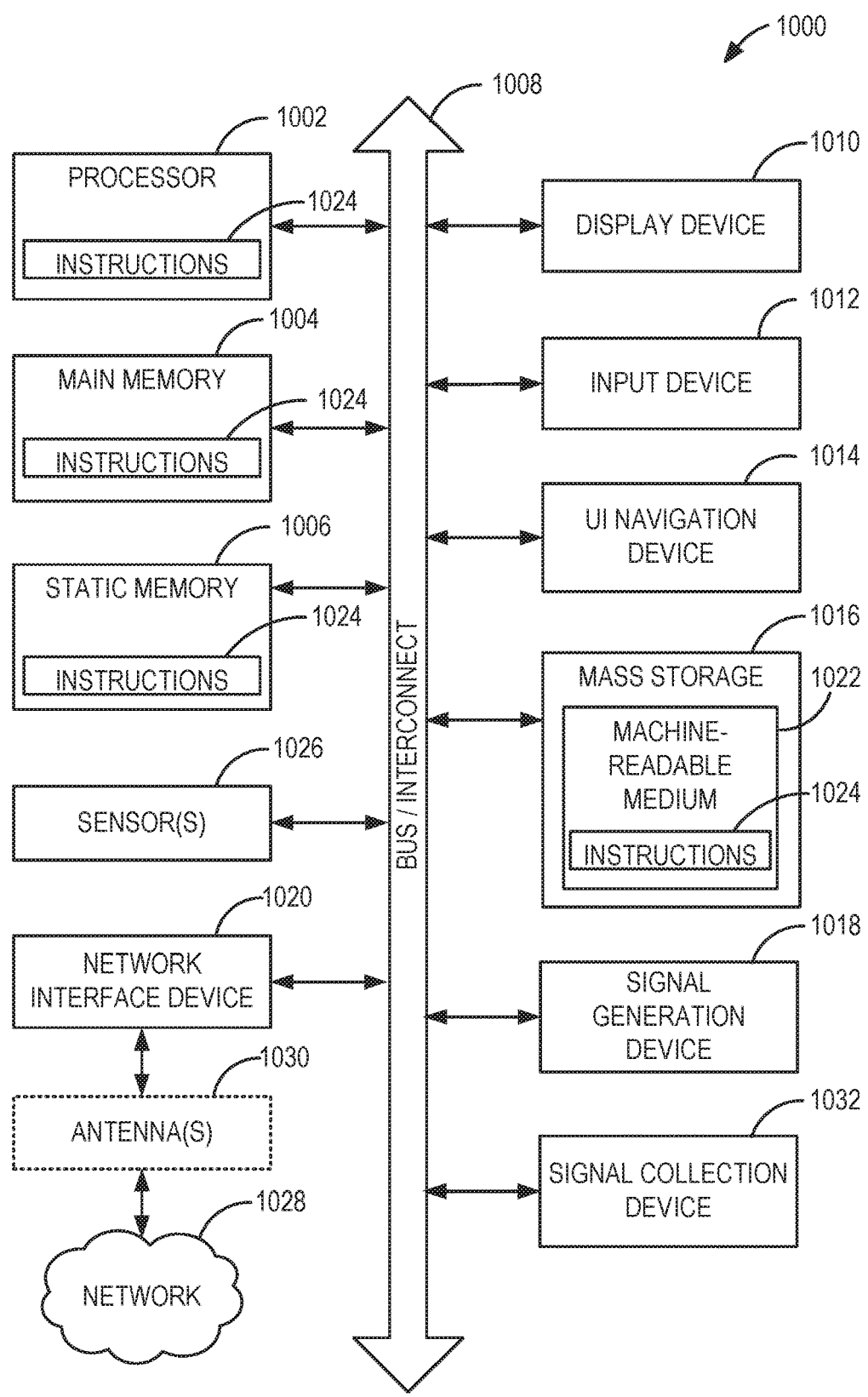
FIG. 10 illustrates an example of a machine configured to perform computing or electronic processing operations according to an example described herein.

FIG. 10 is a block diagram illustrating an example computing system machine upon which any one or more of the methodologies herein discussed may be run. Computer system 1000 may be embodied as a computing device, providing operations of the components featured in the various figures, including components of the modality location 110, 112, 122, the network 120, the workstation location 118, 128, the image data viewer system 910, the image data storage system 920, or the image data generation system 930, or as an execution platform for the operations in the compression approaches 132, 134, the compressor 208 or decompressor 218, the processing and encoding described in FIGS. 3-6B and accompanying text, the flowcharts 700 and 800 in FIGS. 7-8 and accompanying text, or any other processing, storage, or computing platform or component described or referred to herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The computer system machine may be a personal computer (PC) that may or may not be portable (e.g., a notebook or a netbook), a tablet, a Personal Digital Assistant (PDA), a mobile telephone or smartphone, a thin client, a web appliance, a virtual machine host, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 1000 includes a processor 1002 (e.g., a central processing unit (CPU), a graphics processing unit (GPU) or both), a main memory 1004 and a static memory 1006, which communicate with each other via an interconnect 1008 (e.g., a link, a bus, etc.). The computer system 1000 may further include a video display unit 1010, an alphanumeric input device 1012 (e.g., a keyboard), and a user interface (UI) navigation device 1014 (e.g., a mouse). In one example, the video display unit 1010, input device 1012 and UI navigation device 1014 are a touch screen display. The computer system 1000 may additionally include a storage device 1016 (e.g., a drive unit), a signal generation device 1018 (e.g., a speaker), a signal collection device 1032, and a network interface device 1020 (which may include or operably communicate with one or more antennas 1030, transceivers, or other wireless communications hardware), and one or more sensors 1026.

The storage device 1016 includes a machine-readable medium 1022 on which is stored one or more sets of data structures and instructions 1024 (e.g., software) embodying or utilized by any one or more of the methodologies or functions described herein. The instructions 1024 may also reside, completely or at least partially, within the main memory 1004, static memory 1006, and/or within the processor 1002 during execution thereof by the computer system 1000, with the main memory 1004, static memory 1006, and the processor 1002 also constituting machine-readable media.

While the machine-readable medium 1022 is illustrated in an example to be a single medium, the term "machine-readable medium" may include a single medium or multiple media (e.g., a centralized or distributed database, and/or associated caches and servers) that store the one or more instructions 1024. A machine-readable medium includes any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. A machine-readable medium include, but not be limited to, solid-state memories, optical media, and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)), solid state drive (SSD), and flash memory devices; magnetic disks such as internal hard disks and removable disks; magneto-optical disks; and CD-ROM and DVD-ROM disks.

The instructions 1024 may further be transmitted or received over a communications network 1028 using a transmission medium via the network interface device 1020 utilizing any one of a number of well-known transfer protocols (e.g., HTTP). Examples of communication networks include a local area network (LAN), wide area network (WAN), the Internet, mobile telephone networks, Plain Old Telephone (POTS) networks, and wireless data networks (e.g, Wi-Fi, 3G, and 4G LTE/LTE-A, WiMAX, or 5G cellular networks and variations of such networks). Such communications may also be facilitated using any number of personal area networks, LANs, and WANs, using any combination of wired or wireless transmission mediums. A transmission medium thus may include any intangible medium that is capable of providing, encoding, or carrying instructions for execution by the machine, and includes digital or analog communications signals or other intangible medium to facilitate communication of such software.

The embodiments described above may be implemented in one or a combination of hardware, firmware, and software. While some embodiments described herein illustrate only a single machine or device, the terms "system", "apparatus", "machine", or "device" shall also be taken to include any collection of machines or devices that individually or jointly execute a set (or multiple sets) of instructions to perform any one or more of the methodologies discussed herein.

Examples, as described herein, may include, or may operate on, logic or a number of components, modules, or mechanisms. Such components may be tangible entities (e.g., hardware) capable of performing specified operations and may be configured or arranged in a certain manner. In an example, circuits may be arranged (e.g., internally or with respect to external entities such as other circuits) in a specified manner to implement such components. In an example, the whole or part of one or more computer systems (e.g., a standalone, client or server computer system) or one or more hardware processors may be configured by firmware or software (e.g., instructions, an application portion, or an application) that operates to perform specified operations. In an example, the software may reside on a non-transitory machine readable medium (e.g., a machine readable storage device that does not encompass a transitory propagating signal). In an example, the software, when executed by the underlying hardware, causes the hardware to perform the specified operations.

Accordingly, such components may be a tangible entity that is physically constructed, specifically configured (e.g., hardwired), or temporarily (e.g., for a limited period of time) configured or adapted (e.g., programmed or arranged) to operate in a specified manner or to perform part or all of any operation described herein. Considering examples in which such components are temporarily configured, each of the components need not be instantiated at any one moment in time. For example, where the components comprise a hardware processor (e.g., CPU) configured using software, the processor circuitry may be configured as respective different components at different times. Software may accordingly configure hardware processor circuitry, for example, to constitute a particular component at one instance of time and to constitute a different component at a different instance of time.

Additional examples of the presently described method, system, and device embodiments are suggested according to the structures and techniques described above and specified in the following claims.

Example 1 is a method for compression of image data, performed by operations executed with at least one processor of a computing device, with the operations comprising: obtaining a cube of voxels from a three-dimensional image data set; performing a compression technique on the cube of voxels, the compression technique including: generating a subsampled cube of voxels from the cube of voxels; and generating a delta data set from the subsampled cube of voxels, the delta data set indicating differences between voxels in the cube of voxels and the subsampled cube of voxels; and providing the subsampled cube of voxels and the delta data set, wherein the subsampled cube of voxels and the delta data set is operable with a decompression technique to losslessly recreate the cube of voxels.

In Example 2, the subject matter of Example 1 includes, the compression technique including a series of progressive compression techniques performed on the cube of voxels, the progressive compression techniques including: generating a further subsampled cube of voxels from the subsampled cube of voxels; generating a further delta data set from the subsampled cube of voxels, the further delta data set indicating differences between voxels in the subsampled cube of voxels and the further subsampled cube of voxels; and repeating the operations of generating a further subsampled cube of voxels and generating a further delta data set, to produce progressively compressed cubes of voxels and progressively compressed delta data sets from successively subsampled cubes of voxels.

In Example 3, the subject matter of Example 2 includes, the cube of voxels being a N×N×N set of voxels, wherein the subsampled cube of voxels is a (N/2)×(N/2)×(N/2) set of voxels, where N is a power of 2.

In Example 4, the subject matter of Example 3 includes, the cube of voxels being a 32×32×32 set of voxels, wherein the subsampled cube of voxels is a 16×16×16 set of voxels, wherein the progressive compression techniques further produce a 8×8×8 set of voxels, a 4×4×4 set of voxels, a 2×2×2 set of voxels, and a single voxel, from the cube of voxels, wherein the delta data set is produced from differences between the 32×32×32 set of voxels and the 16×16×16 set of voxels, and wherein the further delta data sets are respectively produced from differences between the 16×16×16 set of voxels and the 8×8×8 set of voxels, between the 8×8×8 set of voxels and the 4×4×4 set of voxels, between the 4×4×4 set of voxels and the 2×2×2 set of voxels, and between the 2×2×2 set of voxels and a single voxel.

In Example 5, the subject matter of Example 4 includes, the 32×32×32 set of voxels being a filtered set of voxels, the filtered set of voxels produced from filtering operations including: obtaining a filtered cube of voxels from the three-dimensional image data set, the filtered cube of voxels produced from an original 32×32×32 set of voxels from the three-dimensional image data set; and generating an original delta data set from the filtered cube of voxels, the original delta data set indicating differences between the original 32×32×32 set of voxels and the filtered cube of voxels; wherein the filtered cube of voxels and the original delta data set is operable with the decompression technique to losslessly recreate the original 32×32×32 set of voxels.

In Example 6, the subject matter of Examples 1-5 includes, the subsampled cube of voxels being generated from downsampling the cube of voxels by computing an average value of a plurality of voxels adjacent to the cube of voxels.

In Example 7, the subject matter of Examples 1-6 includes, the delta data set including a plurality of numeric delta values to indicate the differences between voxels in the cube of voxels and the subsampled cube of voxels, wherein the plurality of numeric delta values are represented in the delta data set, for respective numeric delta values, with a non-two's-complement delta representation, and wherein the non-two's-complement delta representation provides a binary representation of an absolute value of an integer for a respective numeric delta value and an indication of a sign of the respective numeric delta value.

In Example 8, the subject matter of Example 7 includes, the indication of the sign of the respective numeric delta value being included in a least significant bit of the binary representation, for each of the respective numeric delta values, and wherein the most significant bits of the binary representation are padded with at least one zero.

In Example 9, the subject matter of Examples 1-8 includes, the compression technique performed on the cube of voxels further including: arranging respective delta values generated from the subsampled cube of voxels in a Morton order; unpacking bit planes of the arranged respective deltas values; and performing an encoding on the unpacked bit planes.

In Example 10, the subject matter of Example 9 includes, the encoding being performed with use of: a zeros-in-frames (ZIF) encoding technique to identify frame locations of zero bytes, or a run-length encoding (RLE) technique to encode runs of zero bytes.

In Example 11, the subject matter of Examples 1-10 includes, the image data being decompressed by: obtaining the subsampled cube of voxels and the delta data set; and applying deltas from the delta data set to the subsampled cube of voxels, to losslessly recreate the cube of voxels.

In Example 12, the subject matter of Example 11 includes, the image data being further decompressed by: decoding unpacked bit planes encoded in the delta data set; packing the bit planes of the decoded bit planes; and arranging delta values of the packed bit planes from a Morton order; wherein the arranged delta values are used in the applied deltas used to losslessly recreate the cube of voxels.

In Example 13, the subject matter of Examples 1-12 includes, the three-dimensional image data set being medical imaging data that represents one or more human anatomical features.

In Example 14, the subject matter of Examples 11-13 includes, the three-dimensional image data being produced from a combination of a plurality of two-dimensional images, wherein the plurality of two-dimensional images are captured by a medical imaging modality.

In Example 15, the subject matter of Examples 1-14 includes, the operations being performed on processor circuitry supporting a single instruction multiple data (SIMD) instruction set, and wherein a size of the cube of voxels is based on a size of the data operable in registers of the processor circuitry with a single instruction of the SIMD instruction set.

Example 16 is at least one machine readable medium including instructions, which when executed by a computing system, cause the computing system to perform any of the methods of Examples 1-15.

Example 17 is an apparatus comprising means for performing any of the methods of Examples 1-15.

Example 18 is a computing system, comprising processing circuitry having at least one processor, the processing circuitry to execute instructions with the at least one processor to compress image data, with the instructions to perform any of the methods of Examples 1-15.

Example 19 is a medical imaging data processing system, comprising processing circuitry having at least one processor, the processing circuitry to execute instructions with the at least one processor to compress image data, with operations that compress three-dimensional medical imaging data, with the instructions to perform any of the methods of Examples 1-15.

Example 20 is a method adapted to compress two-dimensional imaging data, adapting the techniques applied to compress three-dimensional imaging data in any of Examples 1-15.

Example 21 is at least one machine readable medium including instructions, which when executed by a computing system, cause the computing system to compress two-dimensional imaging data, adapting the techniques applied to three-dimensional imaging data in any of Examples 1-15.

Example 22 is an apparatus comprising means for compressing two-dimensional imaging data, using respective means that are adapted to perform the techniques applied to three-dimensional imaging data in any of Examples 1-15.

Example 23 is a computing system, comprising processing circuitry having at least one processor, the processing circuitry to execute instructions with the at least one processor to compress two-dimensional image data, adapting the techniques applied to three-dimensional imaging data in any of Examples 1-15.

Example 24 is a medical imaging data processing system, comprising processing circuitry having at least one processor, the processing circuitry to execute instructions with the at least one processor to compress two-dimensional image data, adapting the techniques applied to three-dimensional imaging data in any of Examples 1-15.

Example 25 is a method for compression of two-dimensional image data, performed by operations executed with at least one processor of a computing device, with the operations comprising: obtaining a N×N set of pixels from a two-dimensional image data set, wherein N is a power of two; performing a compression technique on the set of pixels, the compression technique including: generating a subsampled set of pixels from the set of pixels, wherein the subsampled set of pixels is a (N/2)×(N/2) set of pixels; and generating a delta data set from the subsampled set of pixels, the delta data set indicating differences between pixels in the set of pixels and the subsampled set of pixels; and providing the subsampled set of pixels and the delta data set, wherein the subsampled set of pixels and the delta data set is operable with a decompression technique to losslessly recreate the set of pixels.

In Example 26, the subject matter of Example 25 includes, the compression technique including a series of progressive compression techniques performed on the set of pixels, the progressive compression techniques including: generating a further subsampled set of pixels from the subsampled set of pixels; generating a further delta data set from the subsampled set of pixels, the further delta data set indicating differences between pixels in the subsampled set of pixels and the further subsampled set of pixels; and repeating the operations of generating a further subsampled set of pixels and generating a further delta data set, to produce progressively compressed sets of pixels and progressively compressed delta data sets from successively subsampled sets of pixel.

In Example 27, the subject matter of Examples 25-26 includes, the subsampled set of pixels being generated from downsampling the set of pixels by computing an average value of a plurality of pixels adjacent to the set of pixels.

In Example 28, the subject matter of Examples 25-27 includes, the delta data set including a plurality of numeric delta values to indicate the differences between pixels in the set of pixels and the subsampled set of pixels, wherein the plurality of numeric delta values are represented in the delta data set, for respective numeric delta values, with a non-two's-complement delta representation, and wherein the non-two's-complement delta representation provides a binary representation of an absolute value of an integer for a respective numeric delta value and an indication of a sign of the respective numeric delta value.

In Example 29, the subject matter of Example 28 includes, the indication of the sign of the respective numeric delta value being included in a least significant bit of the binary representation, for each of the respective numeric delta values, and wherein the most significant bits of the binary representation are padded with at least one zero.

In Example 30, the subject matter of Examples 25-29 includes, the compression technique performed on the set of pixels further including: unpacking bit planes of respective delta values generated from the subsampled set of pixels; and performing an encoding on the unpacked bit planes.

In Example 31, the subject matter of Example 30 includes, the encoding being performed with use of: a zeros-in-frames (ZIF) encoding technique to identify frame locations of zero bytes, or a run-length encoding (RLE) technique to encode runs of zero bytes.

In Example 32, the subject matter of Examples 25-31 includes, the image data being decompressed by: obtaining the subsampled set of pixels and the delta data set; and applying deltas from the delta data set to the subsampled set of pixels, to losslessly recreate the set of pixels.

In Example 33, the subject matter of Example 32 includes, the image data being further decompressed by: decoding unpacked bit planes encoded in the delta data set; and packing the bit planes of the decoded bit planes; wherein the delta values of the packed bit planes are used in the applied deltas used to losslessly recreate the set of pixels.

In Example 34, the subject matter of Examples 25-33 includes, the two-dimensional image data set being medical imaging data that represents one or more human anatomical features.

In Example 35, the subject matter of Example 34 includes, wherein the two-dimensional image data is produced from a medical imaging modality.

In Example 36, the subject matter of Examples 25-35 includes, wherein the operations are performed on processor circuitry supporting a single instruction multiple data (SIMD) instruction set, and wherein a size of the set of pixels is based on a size of the data operable in registers of the processor circuitry with a single instruction of the SIMD instruction set.

Example 37 is at least one machine readable medium including instructions, which when executed by a computing system, cause the computing system to perform any of the methods of Examples 25-36.

Example 38 is an apparatus comprising means for performing any of the methods of Examples 25-36.

Example 39 is a computing system, comprising processing circuitry having at least one processor, the processing circuitry to execute instructions with the at least one processor to compress two-dimensional image data, with the instructions to perform any of the methods of Examples 25-36.

Example 40 is a medical imaging data processing system, comprising processing circuitry having at least one processor, the processing circuitry to execute instructions with the at least one processor to compress image data, with operations that compress two-dimensional medical imaging data, with the instructions to perform any of the methods of Examples 25-36.

Other non-limiting examples may be configured to operate separately, or can be combined in any permutation or combination with any one or more of the other examples provided above, in the following claims, or throughout the present disclosure.

What is claimed is:
1. A method for compression of image data, performed by operations executed with at least one processor of a computing device, with the operations comprising:
  obtaining a cube of voxels from a three-dimensional image data set;
  performing a compression technique on the cube of voxels, the compression technique including:
    generating a subsampled cube of voxels from the cube of voxels; and
    generating a delta data set from the subsampled cube of voxels, the delta data set indicating differences between voxels in the cube of voxels and the subsampled cube of voxels; and
    providing the subsampled cube of voxels and the delta data set, wherein the subsampled cube of voxels and the delta data set is operable with a decompression technique to losslessly recreate the cube of voxels.
2. The method of claim 1, wherein the compression technique includes a series of progressive compression techniques performed on the cube of voxels, the progressive compression techniques including:

generating a further subsampled cube of voxels from the subsampled cube of voxels;

generating a further delta data set from the subsampled cube of voxels, the further delta data set indicating differences between voxels in the subsampled cube of voxels and the further subsampled cube of voxels; and repeating the operations of generating a further subsampled cube of voxels and generating a further delta data set, to produce progressively compressed cubes of voxels and progressively compressed delta data sets from successively subsampled cubes of voxels.

3. The method of claim 2, wherein the cube of voxels is a N×N×N set of voxels, and wherein the subsampled cube of voxels is a (N/2)×(N/2)×(N/2) set of voxels, where N is a power of 2.

4. The method of claim 3, wherein the cube of voxels is a 32×32×32 set of voxels, and wherein the subsampled cube of voxels is a 16×16×16 set of voxels, wherein the progressive compression techniques further produce a 8×8×8 set of voxels, a 4×4×4 set of voxels, a 2×2×2 set of voxels, and a single voxel, from the cube of voxels, wherein the delta data set is produced from differences between the 32×32×32 set of voxels and the 16×16×16 set of voxels, and wherein the further delta data sets are respectively produced from differences between the 16×16×16 set of voxels and the 8×8×8 set of voxels, between the 8×8×8 set of voxels and the 4×4×4 set of voxels, between the 4×4×4 set of voxels and the 2×2×2 set of voxels, and between the 2×2×2 set of voxels and a single voxel.

5. The method of claim 4, wherein the 32×32×32 set of voxels is a filtered set of voxels, the filtered set of voxels produced from filtering operations including:

obtaining a filtered cube of voxels from the three-dimensional image data set, the filtered cube of voxels produced from an original 32×32×32 set of voxels from the three-dimensional image data set; and generating an original delta data set from the filtered cube of voxels, the original delta data set indicating differences between the original 32×32×32 set of voxels and the filtered cube of voxels;

wherein the filtered cube of voxels and the original delta data set is operable with the decompression technique to losslessly recreate the original 32×32×32 set of voxels.

6. The method of claim 1, wherein the subsampled cube of voxels is generated from downsampling the cube of voxels by computing an average value of a plurality of voxels adjacent to the cube of voxels.

7. The method of claim 1, wherein the delta data set includes a plurality of numeric delta values to indicate the differences between voxels in the cube of voxels and the subsampled cube of voxels, wherein the plurality of numeric delta values are represented in the delta data set, for respective numeric delta values, with a non-two's-complement delta representation, and wherein the non-two's-complement delta representation provides a binary representation of an absolute value of an integer for a respective numeric delta value and an indication of a sign of the respective numeric delta value.

8. The method of claim 7, wherein the indication of the sign of the respective numeric delta value is included in a least significant bit of the binary representation, for each of the respective numeric delta values, and wherein the most significant bits of the binary representation are padded with at least one zero.

9. The method of claim 1, the compression technique performed on the cube of voxels further including:

arranging respective delta values generated from the subsampled cube of voxels in a Morton order;

unpacking bit planes of the arranged respective deltas values; and performing an encoding on the unpacked bit planes.

10. The method of claim 9, wherein the encoding is performed with use of: a zeros-in-frames (ZIF) encoding technique to identify frame locations of zero bytes, or a run-length encoding (RLE) technique to encode runs of zero bytes.

11. The method of claim 1, wherein the image data is decompressed by:

obtaining the subsampled cube of voxels and the delta data set; and applying deltas from the delta data set to the subsampled cube of voxels, to losslessly recreate the cube of voxels.

12. The method of claim 11, wherein the image data is further decompressed by:

decoding unpacked bit planes encoded in the delta data set;

packing the bit planes of the decoded bit planes; and arranging delta values of the packed bit planes from a Morton order;

wherein the arranged delta values are used in the applied deltas used to losslessly recreate the cube of voxels.

13. The method of claim 1, wherein the three-dimensional image data set is medical imaging data that represents one or more human anatomical features.

14. The method of claim 13, wherein the three-dimensional image data is produced from a combination of a plurality of two-dimensional images, wherein the plurality of two-dimensional images are captured by a medical imaging modality.

15. The method of claim 1, wherein the operations are performed on processor circuitry supporting a single instruction multiple data (SIMD) instruction set, and wherein a size of the cube of voxels is based on a size of the data operable in registers of the processor circuitry with a single instruction of the SIMD instruction set.

16. At least non-transitory machine-readable medium, the machine-readable medium including instructions, which when executed by a machine having a hardware processor, causes the machine to perform operations that:

obtain a cube of voxels from a three-dimensional image data set;

perform a compression technique on the cube of voxels, wherein the compression technique is operable to:

generate a subsampled cube of voxels from the cube of voxels;

generate a delta data set from the subsampled cube of voxels, the delta data set indicating differences between voxels in the cube of voxels and the subsampled cube of voxels; and repeat generation of a subsampled cube of voxels and generation of a delta data set, to produce progressively compressed cubes of voxels and progressively compressed delta data sets from successively subsampled cubes of voxels; and provide the subsampled cube of voxels and the delta data set, wherein the subsampled cube of voxels and the delta data set is operable with a decompression technique to losslessly recreate the cube of voxels.

17. The machine-readable medium of claim 16, the medium further including instructions to perform operations that:
generate the subsampled cube of voxels with a downsampling technique, wherein the downsampling technique computes an average value of a plurality of voxels adjacent to the cube of voxels;
wherein the cube of voxels is a N×N×N set of voxels, and wherein the subsampled cube of voxels is a (N/2)×(N/2)×(N/2) set of voxels, where N is a power of 2.

18. The machine-readable medium of claim 16,
wherein the delta data set includes a plurality of numeric delta values to indicate the differences between voxels in the cube of voxels and the subsampled cube of voxels,
wherein the plurality of numeric delta values are represented in the delta data set, for respective numeric delta values, with a non-two's-complement delta representation,
wherein the non-two's-complement delta representation provides a binary representation of an absolute value of an integer for a respective numeric delta value and an indication of a sign of the respective numeric delta value,
wherein the indication of the sign of the respective delta value is included in a least significant bit of the binary representation, for each of the respective delta values, and
wherein the most significant bits of the binary representation are padded with at least one zero.

19. The machine-readable medium of claim 16, wherein the compression technique performed on the cube of voxels is performed with operations that:
arrange respective delta values generated from the subsampled cube of voxels in a Morton order;
unpack bit planes of the arranged respective delta values; and
perform an encoding on the unpacked bit planes, wherein the encoding is performed with use of: a zeros-in-frames (ZIF) encoding technique to identify frame locations of zero bytes, or a run-length encoding (RLE) technique to encode runs of zero bytes.

20. The machine-readable medium of claim 16, the medium further including instructions to perform operations that:
obtain the subsampled cube of voxels and the delta data set; and
apply deltas from the delta data set to the subsampled cube of voxels, to losslessly recreate the cube of voxels;
wherein the image data is further decompressed by:
decoding unpacked bit planes encoded in the delta data set;
packing the bit planes of the decoded bit planes; and
arranging delta values of the packed bit planes from a Morton order;
wherein the arranged delta values are used in the applied deltas used to losslessly recreate the cube of voxels.

21. The machine-readable medium of claim 16, wherein the image data is decompressed by operations that:
obtain the subsampled cube of voxels and the delta data set; and
apply deltas from the delta data set to the subsampled cube of voxels, to losslessly recreate the cube of voxels.

22. The machine-readable medium of claim 21, wherein the image data is further decompressed by operations that:
decode unpacked bit planes encoded in the delta data set;
pack the bit planes of the decoded bit planes; and
arrange delta values of the packed bit planes from a Morton order;
wherein the arranged delta values are used in the applied deltas used to losslessly recreate the cube of voxels.

23. The machine-readable medium of claim 16, wherein the three-dimensional image data set is medical imaging data that represents one or more human anatomical features, wherein the three-dimensional image data is produced from a combination of a plurality of two-dimensional images, and wherein the plurality of two-dimensional images are captured by a medical imaging modality.

24. A system for compression of image data, the system comprising:
processing circuitry comprising at least one processor; and
a storage medium comprising instructions, which when executed by the at least one processor, cause the processing circuitry to:
obtain a cube of voxels from a three-dimensional image data set; and
perform a compression technique on the cube of voxels, wherein the compression technique is operable to:
generate a subsampled cube of voxels from the cube of voxels;
generate a delta data set from the subsampled cube of voxels, the delta data set indicating differences between voxels in the cube of voxels and the subsampled cube of voxels; and
repeat generation of a subsampled cube of voxels and generation of a delta data set, to produce progressively compressed cubes of voxels and progressively compressed delta data sets from successively subsampled cubes of voxels; and
provide the subsampled cube of voxels and the delta data set, wherein the subsampled cube of voxels and the delta data set is operable with a decompression technique to losslessly recreate the cube of voxels.

25. The system of claim 24, the instructions further to cause the processing circuitry to:
generate the subsampled cube of voxels with a downsampling technique, wherein the downsampling technique computes an average value of a plurality of voxels adjacent to the cube of voxels;
wherein the cube of voxels is a N×N×N set of voxels, and wherein the subsampled cube of voxels is a (N/2)×(N/2)×(N/2) set of voxels, where N is a power of 2.

26. The system of claim 24,
wherein the delta data set includes a plurality of numeric delta values to indicate the differences between voxels in the cube of voxels and the subsampled cube of voxels,
wherein the plurality of numeric delta values are represented in the delta data set, for respective numeric delta values, with a non-two's-complement delta representation,
wherein the non-two's-complement delta representation provides a binary representation of an absolute value of an integer for a respective numeric delta value and an indication of a sign of the respective numeric delta value, wherein the indication of the sign of the respective delta value is included in a least significant bit of the binary representation, for each of the respective delta values, and wherein the most significant bits of the binary representation are padded with at least one zero.

27. The system of claim 24, wherein the compression technique performed on the cube of voxels is performed with operations that:

arrange respective delta values generated from the subsampled cube of voxels in a Morton order;

unpack bit planes of the arranged respective delta values; and perform an encoding on the unpacked bit planes, wherein the encoding is performed with use of: a zeros-in-frames (ZIF) encoding technique to identify frame locations of zero bytes, or a run-length encoding (RLE) technique to encode runs of zero bytes.

28. The system of claim 24, the instructions further to cause the processing circuitry to:

obtain the subsampled cube of voxels and the delta data set; and apply deltas from the delta data set to the subsampled cube of voxels, to losslessly recreate the cube of voxels;

wherein the image data is further decompressed by:
decoding unpacked bit planes encoded in the delta data set;
packing the bit planes of the decoded bit planes; and
arranging delta values of the packed bit planes from a Morton order;
wherein the arranged delta values are used in the applied deltas used to losslessly recreate the cube of voxels.

29. The system of claim 24, wherein the image data is decompressed by operations that:

obtain the subsampled cube of voxels and the delta data set; and apply deltas from the delta data set to the subsampled cube of voxels, to losslessly recreate the cube of voxels.

30. The system of claim 29, wherein the image data is further decompressed by operations that:

decode unpacked bit planes encoded in the delta data set;
pack the bit planes of the decoded bit planes; and
arrange delta values of the packed bit planes from a Morton order;
wherein the arranged delta values are used in the applied deltas used to losslessly recreate the cube of voxels.

31. The system of claim 24, wherein the three-dimensional image data set is medical imaging data that represents one or more human anatomical features, wherein the three-dimensional image data is produced from a combination of a plurality of two-dimensional images, and wherein the plurality of two-dimensional images are captured by a medical imaging modality.

* * * * *